United States Patent
Rockrohr et al.

(10) Patent No.: US 9,364,216 B2
(45) Date of Patent: *Jun. 14, 2016

(54) SURGICAL CLIP APPLIER WITH INTEGRATED CLIP COUNTER

(71) Applicant: Covidien LP, Mansfield, MA (US)

(72) Inventors: Brian Rockrohr, Waterbury, CT (US); Jaroslaw T. Malkowski, Trumbull, CT (US)

(73) Assignee: COVIDIEN LP, Mansfield, MA (US)

( * ) Notice: Subject to any disclaimer, the term of this patent is extended or adjusted under 35 U.S.C. 154(b) by 235 days.

This patent is subject to a terminal disclaimer.

(21) Appl. No.: 13/674,141

(22) Filed: Nov. 12, 2012

(65) Prior Publication Data

US 2013/0172911 A1 Jul. 4, 2013

Related U.S. Application Data

(60) Provisional application No. 61/581,116, filed on Dec. 29, 2011.

(51) Int. Cl.
*A61B 17/10* (2006.01)
*A61B 17/064* (2006.01)
*A61B 17/128* (2006.01)

(52) U.S. Cl.
CPC ........... *A61B 17/064* (2013.01); *A61B 17/1285* (2013.01)

(58) Field of Classification Search
CPC .......................... A61B 17/064; A61B 17/1285
USPC .................................................. 606/142, 143
See application file for complete search history.

(56) References Cited

U.S. PATENT DOCUMENTS

| | | |
|---|---|---|
| 3,120,230 A | 2/1964 | Skold |
| 3,363,628 A | 1/1968 | Wood |
| 3,638,847 A | 2/1972 | Noiles et al. |
| 3,675,688 A | 7/1972 | Bryan et al. |
| 3,867,944 A | 2/1975 | Samuels |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,480,640 A | 11/1984 | Becht |

(Continued)

FOREIGN PATENT DOCUMENTS

| | | |
|---|---|---|
| DE | 20 2009 006113 | 7/2009 |
| EP | 0 073 655 A1 | 3/1983 |

(Continued)

OTHER PUBLICATIONS

The extended European Search Report corresponding to European Application No. EP 07 25 3905.9, completed Jan. 29, 2008; mailed Feb. 7, 2008; (7 Pages).

(Continued)

*Primary Examiner* — Corrine McDermott
*Assistant Examiner* — Sarah Simpson

(57) ABSTRACT

A surgical clip applier is provided including a channel assembly and overlying a clip carrier having a clip counter plate slidably supported in the channel assembly, wherein the clip counter plate is configured and adapted to display a change in status of the clip applier upon actuation of the handle.

14 Claims, 30 Drawing Sheets

(56) References Cited

U.S. PATENT DOCUMENTS

| | | |
|---|---|---|
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,366,458 A | 11/1994 | Korthoff et al. |
| 5,366,459 A | 11/1994 | Yoon |
| 5,368,600 A | 11/1994 | Failla et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |

(56) References Cited

U.S. PATENT DOCUMENTS

| | | |
|---|---|---|
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,522,823 A | 6/1996 | Kuntz et al. |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuildin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A * | 5/1999 | Dicesare et al. ............ 606/143 |
| 5,906,625 A | 5/1999 | Bito et al. |
| 5,913,862 A | 6/1999 | Ramsey et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,017,358 A | 1/2000 | Yoon et al. |
| 6,045,560 A | 4/2000 | McKean et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |

(56) References Cited

U.S. PATENT DOCUMENTS

| | | |
|---|---|---|
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,510,562 B2 | 3/2009 | Lindsay |
| 7,552,853 B2 | 6/2009 | Mas et al. |
| 7,637,917 B2 | 12/2009 | Whitfield et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,248 B2 | 6/2010 | Smith et al. |
| 7,731,724 B2 | 6/2010 | Huitema et al. |
| 7,740,641 B2 | 6/2010 | Huitema |
| 7,752,853 B2 | 7/2010 | Singh et al. |
| 7,753,250 B2 | 7/2010 | Clauson et al. |
| 7,819,886 B2 | 10/2010 | Whitfield et al. |
| 7,887,553 B2 | 2/2011 | Lehman et al. |
| 7,905,890 B2 | 3/2011 | Whitfield et al. |
| 7,942,885 B2 | 5/2011 | Sixto, Jr. et al. |
| 7,988,027 B2 | 8/2011 | Olson |
| 8,011,550 B2 | 9/2011 | Aranyi |
| 8,011,555 B2 | 9/2011 | Tarinelli |
| 8,016,178 B2 | 9/2011 | Olson |
| 8,021,375 B2 | 9/2011 | Aldrich et al. |
| 8,021,378 B2 | 9/2011 | Sixto, Jr. |
| 8,038,686 B2 | 10/2011 | Huitema et al. |
| 8,056,565 B2 | 11/2011 | Zergibel |
| 8,062,310 B2 | 11/2011 | Shibata et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,075,571 B2 | 12/2011 | Vitali et al. |
| 8,080,021 B2 | 12/2011 | Griego |
| 8,083,668 B2 | 12/2011 | Durgin |
| 8,088,061 B2 | 1/2012 | Wells |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,142,451 B2 | 3/2012 | Boulnois |
| 8,157,149 B2 | 4/2012 | Olson |
| 8,157,151 B2 | 4/2012 | Ingmanson |
| 8,172,859 B2 | 5/2012 | Matsuno et al. |
| 8,172,870 B2 | 5/2012 | Shipp |
| 8,187,290 B2 | 5/2012 | Buckman et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema |
| 8,236,012 B2 | 8/2012 | Molitor |
| 8,246,634 B2 | 8/2012 | Huitema |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino |
| 8,267,945 B2 | 9/2012 | Nguyen |
| 8,267,946 B2 | 9/2012 | Whitfield |
| 8,272,554 B2 | 9/2012 | Whitman et al. |
| 8,282,655 B2 | 10/2012 | Whitfield |
| 8,308,743 B2 | 11/2012 | Matsuno et al. |
| 8,328,822 B2 | 12/2012 | Huitema |
| 8,336,556 B2 | 12/2012 | Zergiebel |
| 8,348,130 B2 | 1/2013 | Shah |

(56) References Cited

U.S. PATENT DOCUMENTS

| | | |
|---|---|---|
| 8,357,171 B2 | 1/2013 | Whitfield |
| 8,366,709 B2 | 2/2013 | Schechter et al. |
| 8,366,726 B2 | 2/2013 | Dennis |
| 8,371,491 B2 | 2/2013 | Huitema |
| 8,372,095 B2 | 2/2013 | Viola |
| 8,382,773 B2 | 2/2013 | Whitfield |
| 8,398,655 B2 | 3/2013 | Cheng et al. |
| 8,403,945 B2 | 3/2013 | Whitfield |
| 8,403,946 B2 | 3/2013 | Whitfield |
| 8,408,442 B2 | 4/2013 | Racenet et al. |
| 8,409,222 B2 | 4/2013 | Whitfield |
| 8,409,223 B2 | 4/2013 | Sorrentino |
| 8,419,752 B2 | 4/2013 | Sorrentino |
| 8,430,892 B2 | 4/2013 | Bindra |
| 8,444,660 B2 | 5/2013 | Adams |
| 8,465,460 B2 | 6/2013 | Yodfat et al. |
| 8,465,502 B2 | 6/2013 | Zergiebel |
| 8,475,473 B2 | 7/2013 | Vandenbroek |
| 8,480,688 B2 | 7/2013 | Boulnois |
| 8,486,091 B2 | 7/2013 | Sorrentino |
| 8,491,608 B2 | 7/2013 | Sorrentino |
| 8,496,673 B2 | 7/2013 | Nguyen |
| 8,506,580 B2 | 8/2013 | Zergiebel |
| 8,512,357 B2 | 8/2013 | Viola |
| 8,523,882 B2 | 9/2013 | Huitema |
| 8,529,585 B2 | 9/2013 | Jacobs |
| 8,529,586 B2 | 9/2013 | Rosenberg |
| 8,529,588 B2 | 9/2013 | Ahlberg |
| 8,545,486 B2 | 10/2013 | Malkowski |
| 8,556,920 B2 | 10/2013 | Huitema et al. |
| 8,568,430 B2 | 10/2013 | Shipp |
| 8,579,918 B2 | 11/2013 | Whitfield |
| 8,585,717 B2 | 11/2013 | Sorrentino |
| 8,603,109 B2 | 12/2013 | Aranyi |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,213 B2 | 4/2014 | Shelton, IV et al. |
| 8,709,027 B2 | 4/2014 | Adams et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,920,438 B2 | 12/2014 | Aranyi et al. |
| 8,950,646 B2 | 2/2015 | Viola |
| 8,968,342 B2 | 3/2015 | Wingardner, III et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,186,136 B2 | 11/2015 | Malkowski et al. |
| 9,186,153 B2 | 11/2015 | Zammataro |
| 2001/0047178 A1 | 11/2001 | Peters |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto, Jr. et al. |
| 2002/0198540 A1 | 12/2002 | Smith et al. |
| 2002/0198541 A1 | 12/2002 | Smith et al. |
| 2003/0014060 A1 | 1/2003 | Wilson, Jr. et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake, III |
| 2003/0167063 A1 | 9/2003 | Kerr |
| 2003/0208231 A1 | 11/2003 | Williamson, IV et al. |
| 2003/0220657 A1 | 11/2003 | Adams |
| 2003/0225423 A1 | 12/2003 | Huitema |
| 2003/0229360 A1 | 12/2003 | Gayton |
| 2003/0233105 A1 | 12/2003 | Gayton |
| 2004/0010272 A1 | 1/2004 | Manetakis et al. |
| 2004/0044352 A1 | 3/2004 | Fowler et al. |
| 2004/0097970 A1 | 5/2004 | Hughett |
| 2004/0097971 A1 | 5/2004 | Hughett |
| 2004/0097972 A1 | 5/2004 | Shipp et al. |
| 2004/0106936 A1 | 6/2004 | Shipp et al. |
| 2004/0133215 A1 | 7/2004 | Baxter |
| 2004/0138681 A1 | 7/2004 | Pier |
| 2004/0153100 A1 | 8/2004 | Ahlberg et al. |
| 2004/0158266 A1 | 8/2004 | Damarati |
| 2004/0162567 A9 | 8/2004 | Adams |
| 2004/0167545 A1 | 8/2004 | Sadler et al. |
| 2004/0176776 A1 | 9/2004 | Zubok et al. |
| 2004/0176783 A1 | 9/2004 | Edoga et al. |
| 2004/0176784 A1 | 9/2004 | Okada |
| 2004/0193213 A1 | 9/2004 | Aranyi |
| 2005/0080440 A1 | 4/2005 | Durgin et al. |
| 2005/0085830 A1 | 4/2005 | Lehman et al. |
| 2005/0090837 A1 | 4/2005 | Sixto, Jr. et al. |
| 2005/0090838 A1 | 4/2005 | Sixto, Jr. et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0175703 A1 | 8/2005 | Hunter |
| 2005/0177176 A1 | 8/2005 | Gerbi et al. |
| 2005/0177177 A1 | 8/2005 | Viola |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |

(56) References Cited

U.S. PATENT DOCUMENTS

| | | |
|---|---|---|
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake, III et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi et al. |
| 2006/0079912 A1 | 4/2006 | Whitfield et al. |
| 2006/0079913 A1 | 4/2006 | Whitfield et al. |
| 2006/0085015 A1 | 4/2006 | Whitfield et al. |
| 2006/0100649 A1 | 5/2006 | Hart |
| 2006/0111731 A1 | 5/2006 | Manzo |
| 2006/0129170 A1 | 6/2006 | Royce et al. |
| 2006/0135992 A1 | 6/2006 | Bettuchi et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0212050 A1 | 9/2006 | D'Agostino et al. |
| 2006/0217749 A1 | 9/2006 | Wilson, Jr. et al. |
| 2006/0224165 A1 | 10/2006 | Surti |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | De La Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0066981 A1 | 3/2007 | Meagher |
| 2007/0073314 A1 | 3/2007 | Gadberry et al. |
| 2007/0083218 A1 | 4/2007 | Morris |
| 2007/0093856 A1 | 4/2007 | Whitfield et al. |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto, Jr. et al. |
| 2007/0149988 A1 | 6/2007 | Michler et al. |
| 2007/0149989 A1 | 6/2007 | Santili et al. |
| 2007/0162060 A1 | 7/2007 | Wild |
| 2007/0173866 A1 | 7/2007 | Sorrentino et al. |
| 2007/0175949 A1 | 8/2007 | Shelton et al. |
| 2007/0185504 A1 | 8/2007 | Manetakis et al. |
| 2007/0191868 A1 | 8/2007 | Theroux et al. |
| 2007/0203509 A1 | 8/2007 | Bettuchi |
| 2007/0203510 A1 | 8/2007 | Bettuchi |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0065119 A1 | 3/2008 | Viola |
| 2008/0140090 A1 | 6/2008 | Aranyi et al. |
| 2008/0147092 A1 | 6/2008 | Rogge et al. |
| 2008/0147093 A1 | 6/2008 | Roskopf et al. |
| 2008/0154287 A1 | 6/2008 | Rosenberg et al. |
| 2008/0167665 A1 | 7/2008 | Arp et al. |
| 2008/0167671 A1 | 7/2008 | Giordano et al. |
| 2008/0228199 A1 | 9/2008 | Cropper et al. |
| 2008/0243145 A1 | 10/2008 | Whitfield et al. |
| 2008/0255413 A1 | 10/2008 | Zemlok et al. |
| 2008/0306492 A1 | 12/2008 | Shibata et al. |
| 2008/0306493 A1 | 12/2008 | Shibata et al. |
| 2008/0312665 A1 | 12/2008 | Shibata et al. |
| 2008/0312670 A1 | 12/2008 | Lutze et al. |
| 2008/0319456 A1 | 12/2008 | Hart |
| 2009/0076533 A1 | 3/2009 | Kayan et al. |
| 2009/0088777 A1 | 4/2009 | Miyagi et al. |
| 2009/0088783 A1 | 4/2009 | Kennedy et al. |
| 2009/0171380 A1 | 7/2009 | Whiting |
| 2009/0222003 A1 | 9/2009 | Otley et al. |
| 2009/0228023 A1 | 9/2009 | Cui et al. |
| 2009/0228024 A1 | 9/2009 | Whitfield et al. |
| 2009/0264904 A1 | 10/2009 | Aldrich et al. |
| 2009/0299382 A1 | 12/2009 | Zergiebel |
| 2009/0326558 A1 | 12/2009 | Cui et al. |
| 2010/0049216 A1* | 2/2010 | Zergiebel ............ 606/143 |
| 2010/0057102 A1 | 3/2010 | Sorrentino et al. |
| 2010/0057103 A1 | 3/2010 | Sorrentino et al. |
| 2010/0057104 A1 | 3/2010 | Sorrentino et al. |
| 2010/0057105 A1 | 3/2010 | Sorrentino et al. |
| 2010/0057106 A1 | 3/2010 | Sorrentino et al. |
| 2010/0057107 A1 | 3/2010 | Sorrentino et al. |
| 2010/0069935 A1 | 3/2010 | Crainich |
| 2010/0121351 A1 | 5/2010 | Whitfield |
| 2010/0137886 A1 | 6/2010 | Zergiebel |
| 2010/0204715 A1 | 8/2010 | Whitfield et al. |
| 2010/0222790 A1 | 9/2010 | Whitfield et al. |
| 2010/0274262 A1 | 10/2010 | Schulz et al. |
| 2010/0274264 A1 | 10/2010 | Schulz et al. |
| 2011/0028994 A1 | 2/2011 | Whitfield et al. |
| 2011/0054498 A1 | 3/2011 | Monassevitch et al. |
| 2011/0082474 A1 | 4/2011 | Bindra et al. |
| 2011/0087241 A1 | 4/2011 | Nguyen |
| 2011/0087242 A1 | 4/2011 | Pribanic et al. |
| 2011/0087243 A1 | 4/2011 | Nguyen et al. |
| 2011/0112552 A1 | 5/2011 | Lehman et al. |
| 2011/0137323 A1 | 6/2011 | Malkowski et al. |
| 2011/0137324 A1 | 6/2011 | Boudreaux et al. |
| 2011/0144662 A1 | 6/2011 | McLawhorn et al. |
| 2011/0144665 A1 | 6/2011 | Malkowski |
| 2011/0190791 A1 | 8/2011 | Jacobs et al. |
| 2011/0208211 A1 | 8/2011 | Whitfield et al. |
| 2011/0208212 A1 | 8/2011 | Zergiebel et al. |
| 2011/0218553 A1 | 9/2011 | Huitema et al. |
| 2011/0218554 A1 | 9/2011 | Cheng et al. |
| 2011/0218555 A1 | 9/2011 | Huitema |
| 2011/0218556 A1 | 9/2011 | Nguyen et al. |
| 2011/0224696 A1 | 9/2011 | Huitema et al. |
| 2011/0224700 A1 | 9/2011 | Schmidt et al. |
| 2011/0224701 A1 | 9/2011 | Menn |

(56) References Cited

U.S. PATENT DOCUMENTS

| | | |
|---|---|---|
| 2011/0230900 A1 | 9/2011 | Sarradon |
| 2011/0245847 A1 | 10/2011 | Menn et al. |
| 2011/0245848 A1 | 10/2011 | Rosenberg et al. |
| 2011/0251608 A1 | 10/2011 | Timm et al. |
| 2011/0295290 A1 | 12/2011 | Whitfield |
| 2011/0313437 A1 | 12/2011 | Yeh |
| 2012/0029533 A1 | 2/2012 | Whitfield et al. |
| 2012/0029534 A1 | 2/2012 | Whitfield et al. |
| 2012/0041455 A1 | 2/2012 | Martinez |
| 2012/0042497 A1 | 2/2012 | Zergiebel |
| 2012/0046671 A1 | 2/2012 | Matsuoka et al. |
| 2012/0059394 A1 | 3/2012 | Brenner et al. |
| 2012/0065647 A1 | 3/2012 | Litscher et al. |
| 2012/0109158 A1 | 5/2012 | Zammataro |
| 2012/0116420 A1 | 5/2012 | Sorrentino |
| 2012/0123446 A1 | 5/2012 | Aranyi |
| 2012/0197269 A1 | 8/2012 | Zammataro |
| 2012/0265220 A1 | 10/2012 | Menn |
| 2012/0277765 A1 | 11/2012 | Zammataro |
| 2012/0330326 A1 | 12/2012 | Creston |
| 2013/0110135 A1 | 5/2013 | Whitfield |
| 2013/0131697 A1 | 5/2013 | Hartoumbekis |
| 2013/0165952 A1 | 6/2013 | Whitfield |
| 2013/0172910 A1 | 7/2013 | Malkowski |
| 2013/0172911 A1 | 7/2013 | Rockrohr |
| 2013/0172912 A1 | 7/2013 | Whitfield |
| 2013/0190779 A1 | 7/2013 | Whitfield |
| 2013/0190780 A1 | 7/2013 | Whitfield |
| 2013/0253541 A1 | 9/2013 | Zergiebel |
| 2013/0274767 A1 | 10/2013 | Sorrentino |
| 2013/0289583 A1 | 10/2013 | Zergiebel |
| 2013/0296891 A1 | 11/2013 | Hartoumbekis |
| 2013/0296892 A1 | 11/2013 | Sorrentino |
| 2013/0310849 A1 | 11/2013 | Malkowski |
| 2013/0325040 A1 | 12/2013 | Zammataro |
| 2014/0039526 A1 | 2/2014 | Malkowski |
| 2014/0052157 A1 | 2/2014 | Whitfield |
| 2014/0058412 A1 | 2/2014 | Aranyi |
| 2014/0194903 A1 | 7/2014 | Malkowski et al. |
| 2014/0207156 A1 | 7/2014 | Malkowski |
| 2014/0316441 A1 | 10/2014 | Zergiebel et al. |
| 2015/0005790 A1 | 1/2015 | Whitfield et al. |
| 2015/0045816 A1 | 2/2015 | Aranyi et al. |
| 2015/0164511 A1 | 6/2015 | Whitfield et al. |
| 2015/0190138 A1 | 7/2015 | Whitfield et al. |
| 2015/0190139 A1 | 7/2015 | Zammataro |
| 2015/0282808 A1 | 10/2015 | Sorrentino et al. |
| 2015/0351771 A1 | 12/2015 | Malkowski et al. |
| 2015/0351772 A1 | 12/2015 | Malkowski et al. |

FOREIGN PATENT DOCUMENTS

| | | |
|---|---|---|
| EP | 0 085 931 A2 | 8/1983 |
| EP | 0 086 721 | 8/1983 |
| EP | 0 089 737 A1 | 9/1983 |
| EP | 0 092 300 A1 | 10/1983 |
| EP | 0 324 166 A2 | 7/1989 |
| EP | 0 392 750 A1 | 10/1990 |
| EP | 0 406 724 A1 | 1/1991 |
| EP | 0 409 569 A1 | 1/1991 |
| EP | 0 569 223 | 11/1993 |
| EP | 0 594 003 | 4/1994 |
| EP | 0 598 529 A2 | 5/1994 |
| EP | 0 685 204 A1 | 12/1995 |
| EP | 0 732 078 A2 | 9/1996 |
| EP | 0 755 655 A2 | 1/1997 |
| EP | 0 769 274 | 4/1997 |
| EP | 0 769 274 A1 | 4/1997 |
| EP | 0 769 275 A1 | 4/1997 |
| EP | 0 834 286 A1 | 4/1998 |
| EP | 1 317 906 A1 | 6/2003 |
| EP | 1 609 427 A1 | 12/2005 |
| EP | 1 712 187 | 10/2006 |
| EP | 1 712 191 A2 | 10/2006 |
| EP | 1 757 236 | 2/2007 |
| EP | 1 813 199 A1 | 8/2007 |
| EP | 1 908 423 | 4/2008 |
| EP | 1 908 423 A2 | 4/2008 |
| EP | 1 913 881 A1 | 4/2008 |
| EP | 2 229 895 A1 | 9/2010 |
| EP | 2 332 471 | 6/2011 |
| JP | 2003 033361 A | 2/2003 |
| WO | WO 01/66001 | 9/2001 |
| WO | WO 01/67965 | 9/2001 |
| WO | WO 03/086207 | 10/2003 |
| WO | WO 03/092473 | 11/2003 |
| WO | WO 2005/091457 A1 | 9/2005 |
| WO | WO 2006/042076 | 4/2006 |
| WO | WO 2006/042076 A2 | 4/2006 |
| WO | WO 2006/042084 A2 | 4/2006 |
| WO | WO 2006/042110 | 4/2006 |
| WO | WO 2006/042110 A2 | 4/2006 |
| WO | WO 2006/042141 | 4/2006 |
| WO | WO 2006/135479 | 12/2006 |
| WO | WO 2008/118928 | 10/2008 |
| WO | WO 2008/118928 A2 | 10/2008 |
| WO | WO 2008/127968 | 10/2008 |
| WO | WO 2008/127968 A2 | 10/2008 |

OTHER PUBLICATIONS

The partial European Search Report corresponding to European Application No. EP 07 25 3807.7, completed Jul. 23, 2008; mailed Aug. 1, 2008; (3 pages).

International Search Report corresponding to International Application No. PCT/US08/58185, completed Sep. 4, 2008; mailed Sep. 9, 2008; (2 Pages).

The International Search Report corresponding to International Application No. PCT/US08/59859, completed Sep. 14, 2008; mailed Sep. 18, 2008; (2 Pages).

The extended European Search Report corresponding to European Application No. EP 07 25 3807.7, completed Nov. 7, 2008; mailed Nov. 26, 2008; (11 Pages).

The extended European Search Report corresponding to European Application No. EP 09 25 2049.3, completed Dec. 11, 2009; mailed Jan. 12, 2010; (3 Pages).

The extended European Search Report corresponding to European Application No. EP 09 25 2050.1, completed Dec. 23, 2009; mailed Jan. 21, 2010; (3 Pages).

The extended European Search Report corresponding to European Application No. EP 09 25 2051.9, completed Dec. 21, 2009; mailed Jan. 28, 2010; (3 Pages).

The extended European Search Report corresponding to European Application No. EP 09 25 2052.7, completed Nov. 16, 2009; mailed Nov. 24, 2009; (3 Pages).

The extended European Search Report corresponding to European Application No. EP 09 25 2053.5, completed Nov. 24, 2009; mailed Dec. 1, 2009; (3 Pages).

The extended European Search Report corresponding to European Application No. EP 09 25 2054.3, completed Jan. 7, 2010; mailed Jan. 22, 2010; (3 Pages).

The extended European Search Report corresponding to European Application No. EP 09 25 2056.8, completed Jan. 8, 2010; mailed Feb. 5, 2010; (3 Pages).

The extended European Search Report corresponding to European Application No. EP 10 25 0497.4, completed May 4, 2010; mailed May 12, 2010; (6 Pages).

The extended European Search Report corresponding to European Application No. EP 10 25 2079.8, completed Mar. 8, 2011; mailed Mar. 17, 2011; (3 Pages).

The European Search Report corresponding to European Application No. EP 05 81 0218.7, completed Apr. 18, 2011; mailed May 20, 2011; (3 pages).

The European Search Report corresponding to European Application No. EP 05 80 7612.6, completed May 2, 2011; mailed May 20, 2011; (3 pages).

The extended European Search Report corresponding to European Application No. EP 10 25 1737.2, completed May 9, 2011; mailed May 20, 2011; (4 pages).

(56) References Cited

OTHER PUBLICATIONS

The extended European Search Report corresponding to European Application No. EP 11 00 2681.2, completed May 31, 2011; mailed Jun. 10, 2011; (3 Pages).
The extended European Search Report corresponding to European Application No. EP 11 25 0214.1, completed May 25, 2011; mailed Jun. 1, 2011; (3 Pages).
The European Search Report corresponding to European Application No. EP 05 80 2686.5, completed Jan. 9, 2012; mailed Jan. 18, 2012; (3 Pages).
The extended European Search Report corresponding to European Application No. EP 12 15 1313.9, completed Mar. 20, 2012 and mailed Apr. 12, 2012; (5 Pages).
The extended European Search Report corresponding to European Application No. EP 12 16 1291.5, completed Apr. 24, 2012 and mailed May 4, 2012; (5 Pages).
The extended European Search Report corresponding to European Application No. EP 12 16 2288.0, completed Jun. 4, 2012 and mailed Jul. 7, 2012; (6 Pages).
The extended European Search Report corresponding to European Application No. EP 12 16 5891.8, completed Jun. 12, 2012 and mailed Jun. 20, 2012; (6 Pages).
The extended European Search Report corresponding to European Application No. EP 12 16 4955.2, completed Aug. 23, 2012 and mailed Sep. 4, 2012; (5 Pages).
The extended European Search Report corresponding to European Application No. EP 11 25 0754.6, completed Oct. 22, 2012 and mailed Oct. 31, 2012; (6 Pages).
The extended European Search Report corresponding to European Application No. EP 12 18 6448.2, completed Nov. 28, 2012 and mailed Dec. 10, 2012; (6 Pages).
The extended European Search Report corresponding to European Application No. EP 12 18 6401.1, completed Nov. 22, 2012 and mailed Nov. 30, 2012; (7 Pages).
The extended European Search Report corresponding to European Application No. EP 12 19 1706.6, completed Dec. 19, 2012 and mailed Jan. 8, 2013; (6 Pages).
"Salute II Disposable Fixation Device", Technique Guide—Laparoscopic and Open Inguinal and Ventral Hernia Repair; Davol, A Bard Company, 2006; (7 Pages).
Extended European Search Report corresponding to EP 10 25 2112.7, completed Jul. 29, 2014 and mailed Aug. 5, 2014; (8 pp).
Extended European Search Report corresponding to EP 14 15 1673.2, completed Apr. 25, 2014 and mailed May 8, 2014; (8 pp).
Extended European Search Report corresponding to EP 12 15 2989.5, completed Apr. 9, 2013 and mailed Apr. 18, 2013; (9 pp).
Extended European Search Report corresponding to EP 08 73 2820.9, completed Jul. 2, 2013 and mailed Jul. 9, 2013; (10 pp).
Extended European Search Report corresponding to EP 12 19 1706.6, completed Dec. 19, 2012 and mailed Jan. 8, 2013; (6 pp).
Extended European Search Report corresponding to EP 13 17 2008.8, completed Aug. 14, 2013 and mailed Aug. 28, 2013; (8 pp).
Extended European Search Report corresponding to EP 12 19 8745.7, completed Mar. 19, 2013 and mailed Apr. 11, 2013; (22 pp).
Extended European Search Report corresponding to EP 13 16 6382.5, completed Nov. 19, 2013 and mailed Nov. 28, 2013; (8 pp).
Extended European Search Report corresponding to EP 11 25 0194.5, completed Nov. 25, 2013 and mailed Dec. 3, 2013; (8 pp).
Extended European Search Report corresponding to EP 10 25 1798.4, completed Dec. 12, 2013 and mailed Jan. 2, 2014; (9 pp).
Chinese Office Action corresponding to counterpart Int'l Appln No. CN 201210212642.9 dated Jun. 3, 2015.
European Office Action corresponding to counterpart Int'l Appln No. EP 04 719 757.9 dated Jun. 12, 2015.
European Office Action corresponding to counterpart Int'l Appln No. EP 13 166 382.5 dated Jun. 19, 2015.
Japanese Office Action corresponding to counterpart Int'l Application No. JP 2010-226908 dated Jun. 26, 2015.
Extended European Search Report corresponding to counterpart Int'l Application No. EP 15 15 5024.1 dated Jul. 17, 2015.
Extended European Search Report corresponding to counterpart Int'l Application No. EP 14 19 2026.4 dated Jul. 17, 2015.
Japanese Office Action corresponding to counterpart Int'l Application No. JP 2011-160126 dated Aug. 10, 2015.
Extended European Search Report corresponding to counterpart Int'l Application No. EP 14 15 0321.9 dated Sep. 23, 2015.
Extended European Search Report corresponding to counterpart Int'l Application No. EP 11 25 0675.3 dated Oct. 7, 2015.
Extended European Search Report corresponding to counterpart Int'l Application No. EP 11 25 0674.6 dated Oct. 7, 2015.
Extended European Search Report corresponding to counterpart Int'l Application No. EP 12 19 3447.5 dated Oct. 19, 2015.
Canadian Office Action corresponding to counterpart Int'l Application No. CA 2,675,875 dated Oct. 26, 2015.
Japanese Office Action corresponding to counterpart Int'l Application No. JP 2015-005629 dated Oct. 28, 2015.
Japanese Office Action corresponding to counterpart Int'l Application No. JP 2014-245081 dated Oct. 28, 2015.
Canadian Office Action corresponding to counterpart Int'l Application No. CA 2,675,921 dated Oct. 30, 2015.
Chinese Office Action corresponding to counterpart Int'l Application No. CN 201210555570.8 dated Nov. 2, 2015.
Canadian Office Action corresponding to counterpart Int'l Application No. CA 2,676,309 dated Nov. 3, 2015.
Canadian Office Action corresponding to counterpart Int'l Application No. CA 2,676,211 dated Nov. 24, 2015.
Canadian Office Action corresponding to counterpart Int'l Application No. CA 2,676,547 dated Nov. 25, 2015.
Extended European Search Report corresponding to counterpart Int'l Application No. EP 15 17 3809.3 dated Nov. 25, 2015.
Chinese Office Action corresponding to counterpart Int'l Application No. CN 201210586814.9 dated Dec. 2, 2015.
Extended European Search Report corresponding to counterpart Int'l Application No. EP 12 17 2940.4 dated Dec. 14, 2015.
Japanese Office Action (in Japanese and English) corresponding to counterpart Int'l Appln. No. JP 201210586814.9 dated Dec. 2, 2015; (21 pp).

* cited by examiner

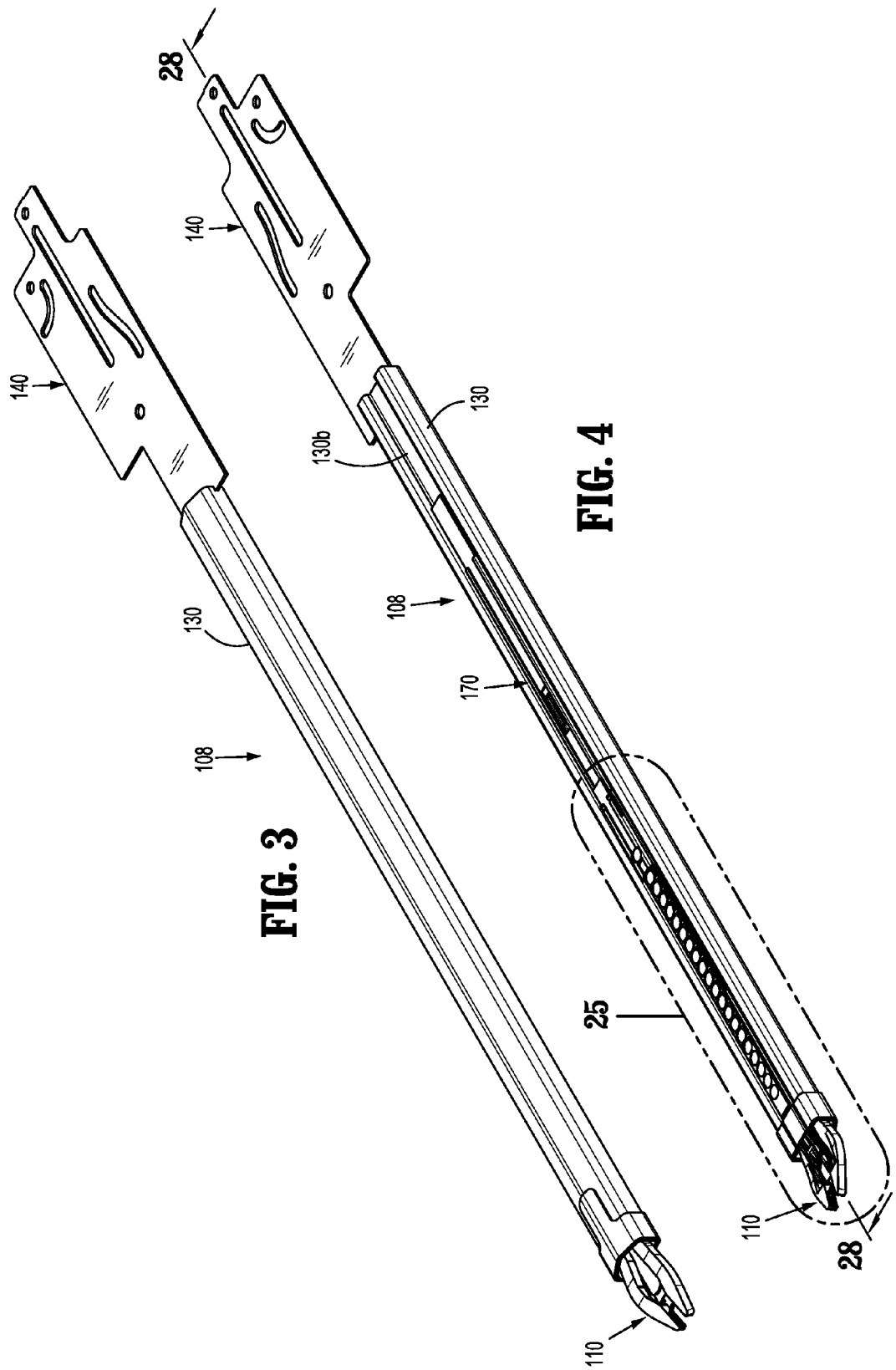

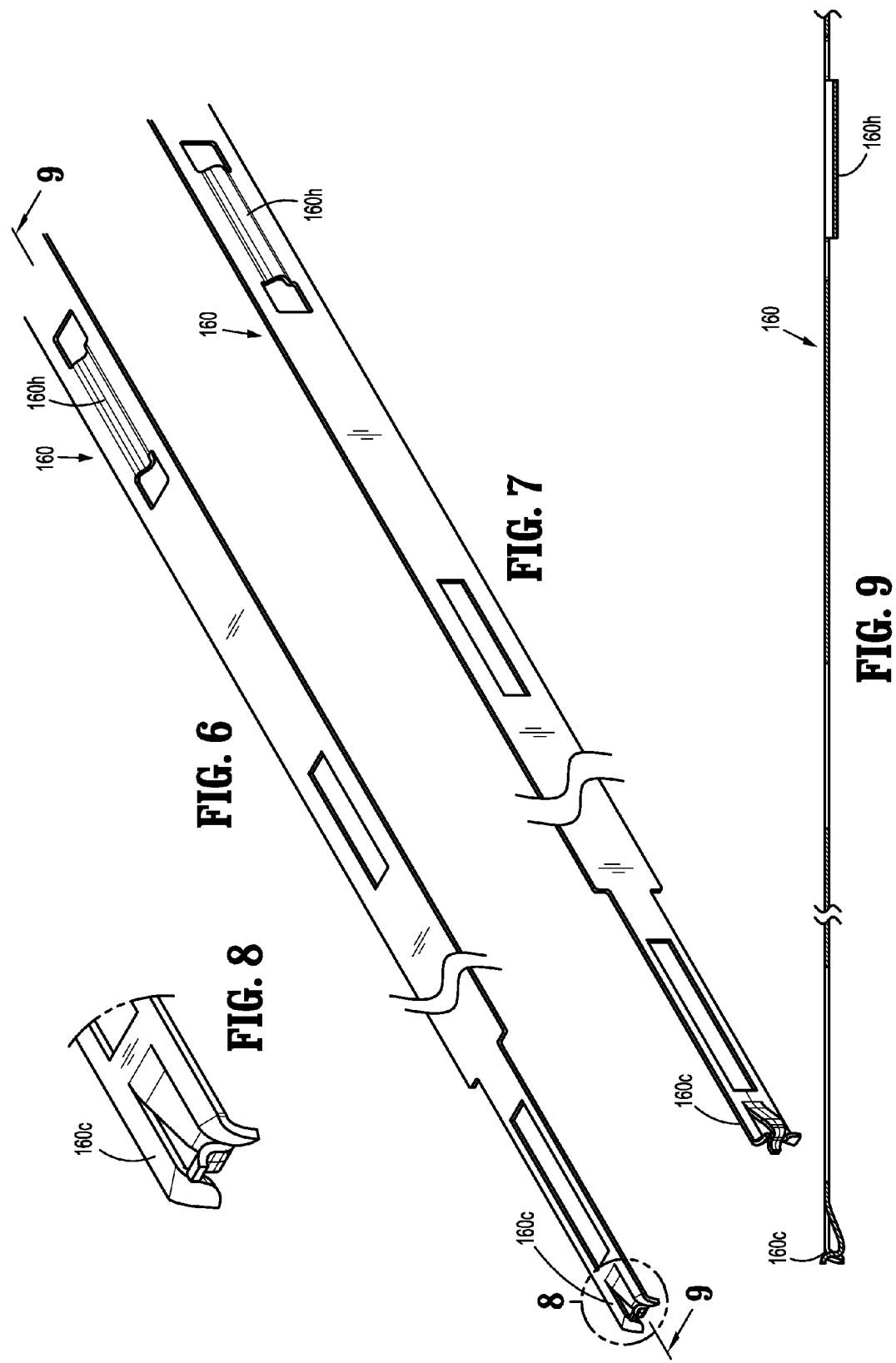

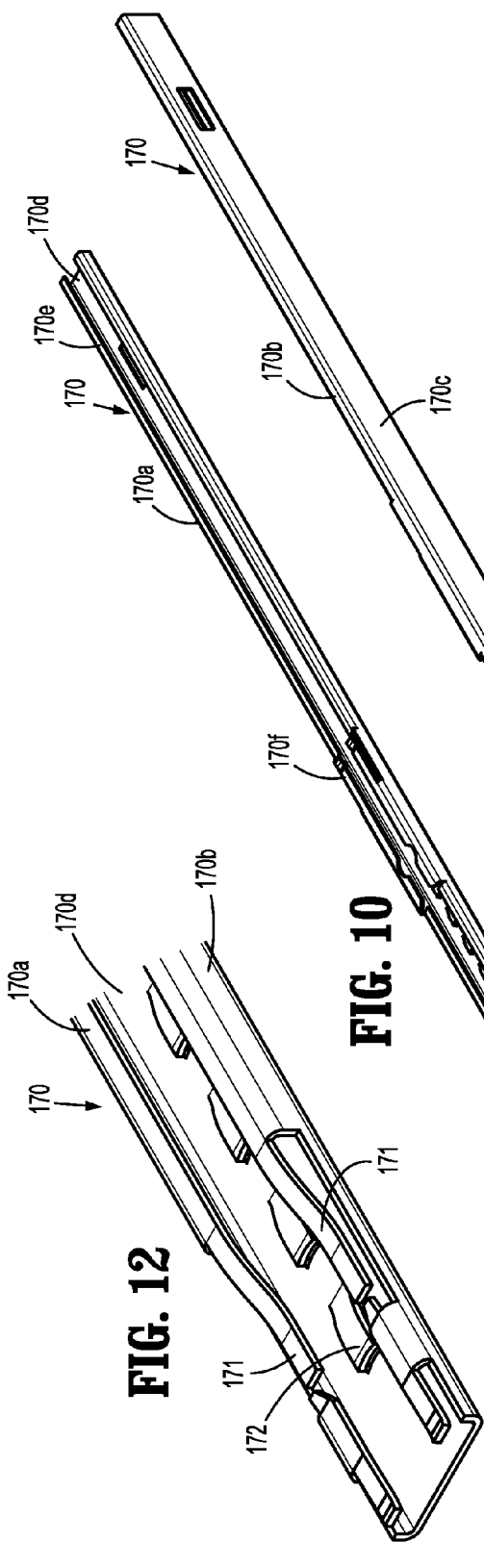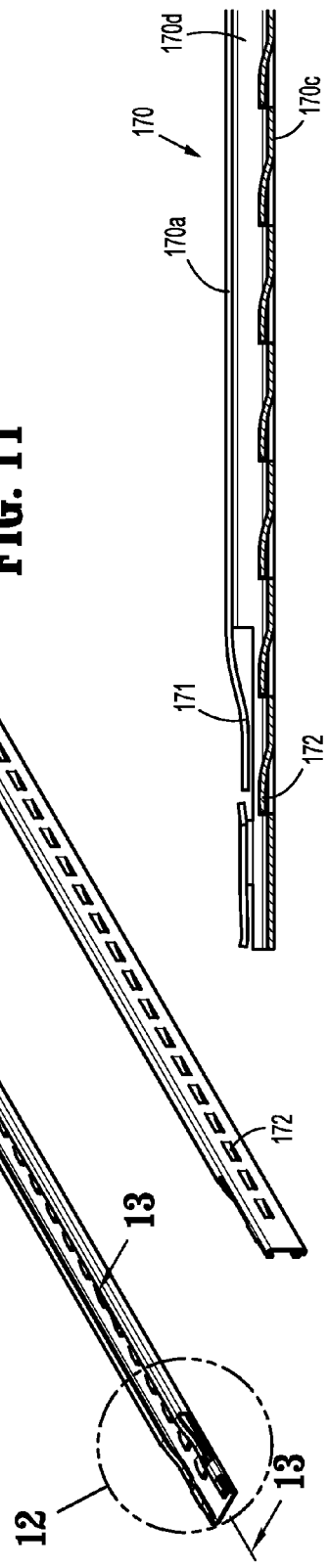

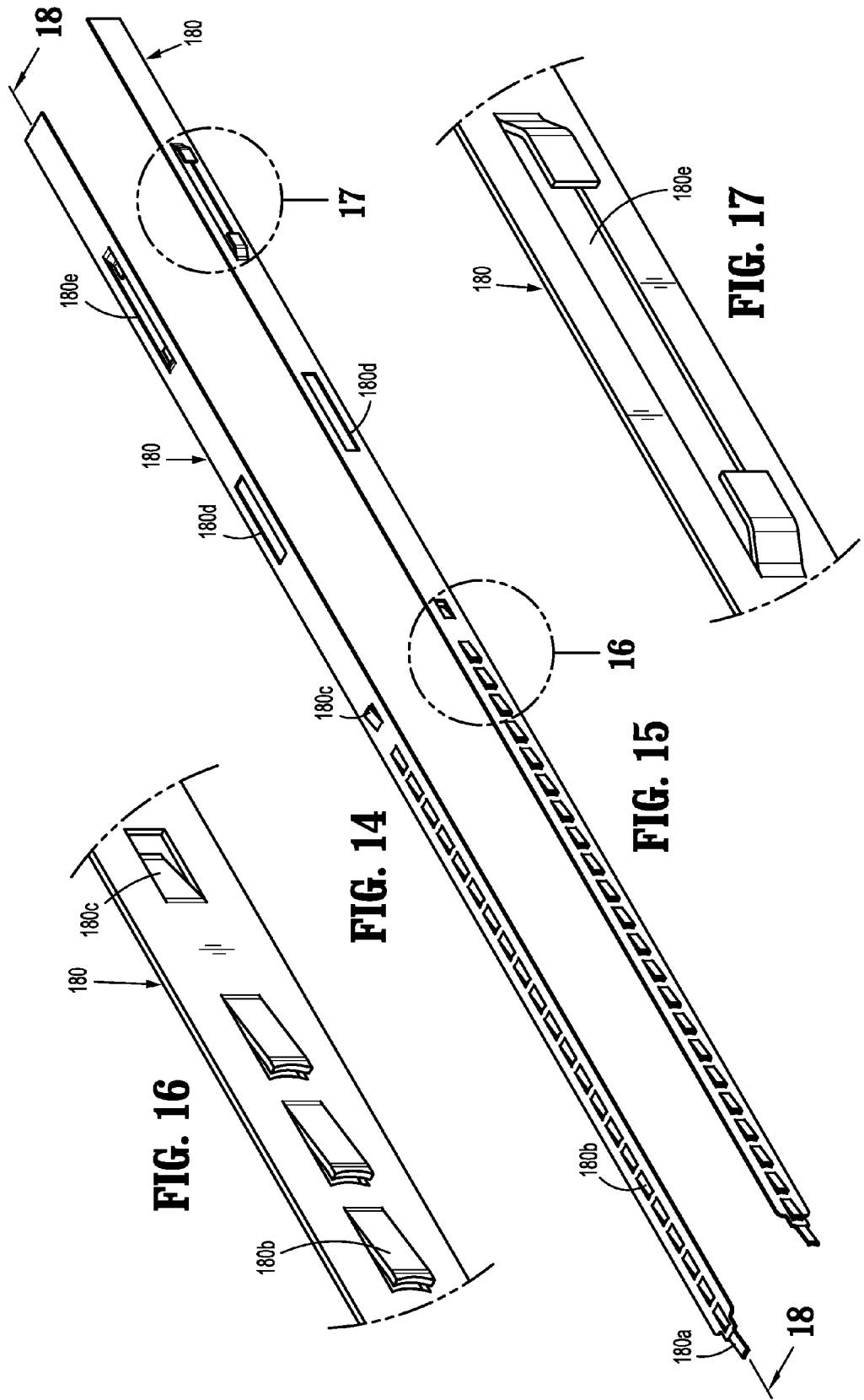

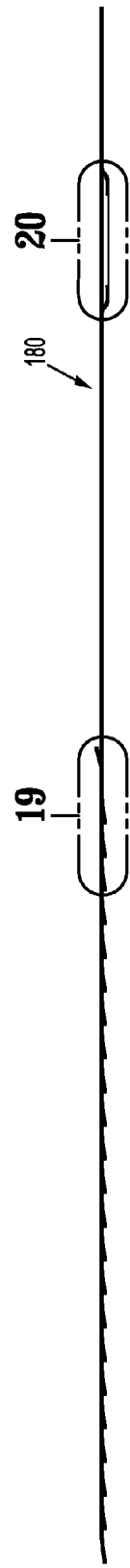
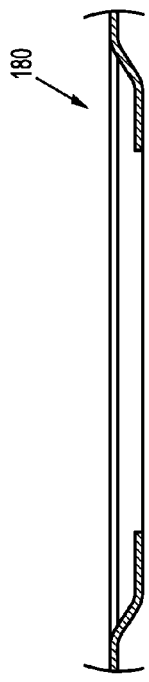
FIG. 18
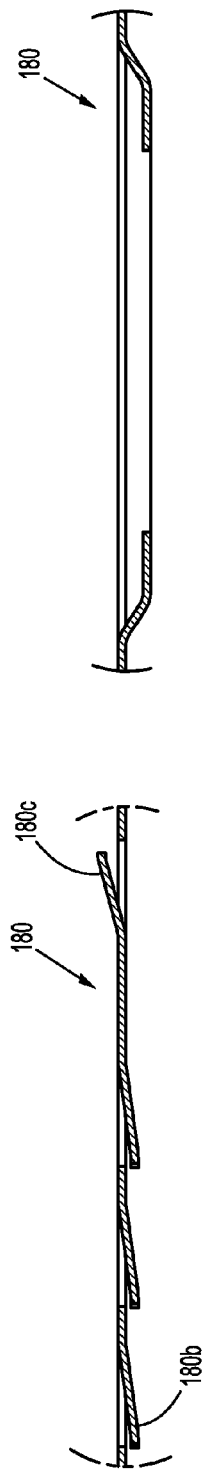
FIG. 19
FIG. 20

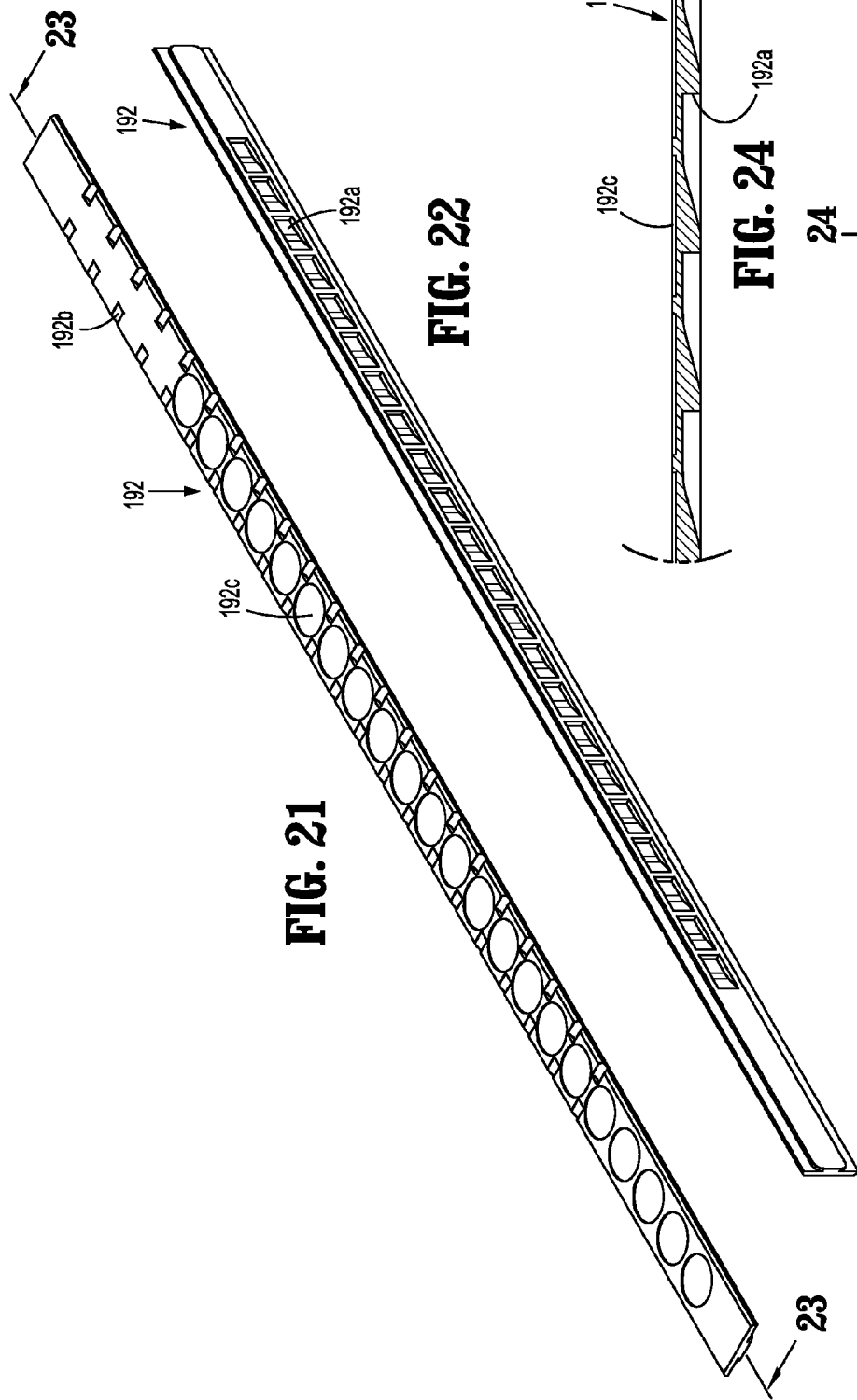

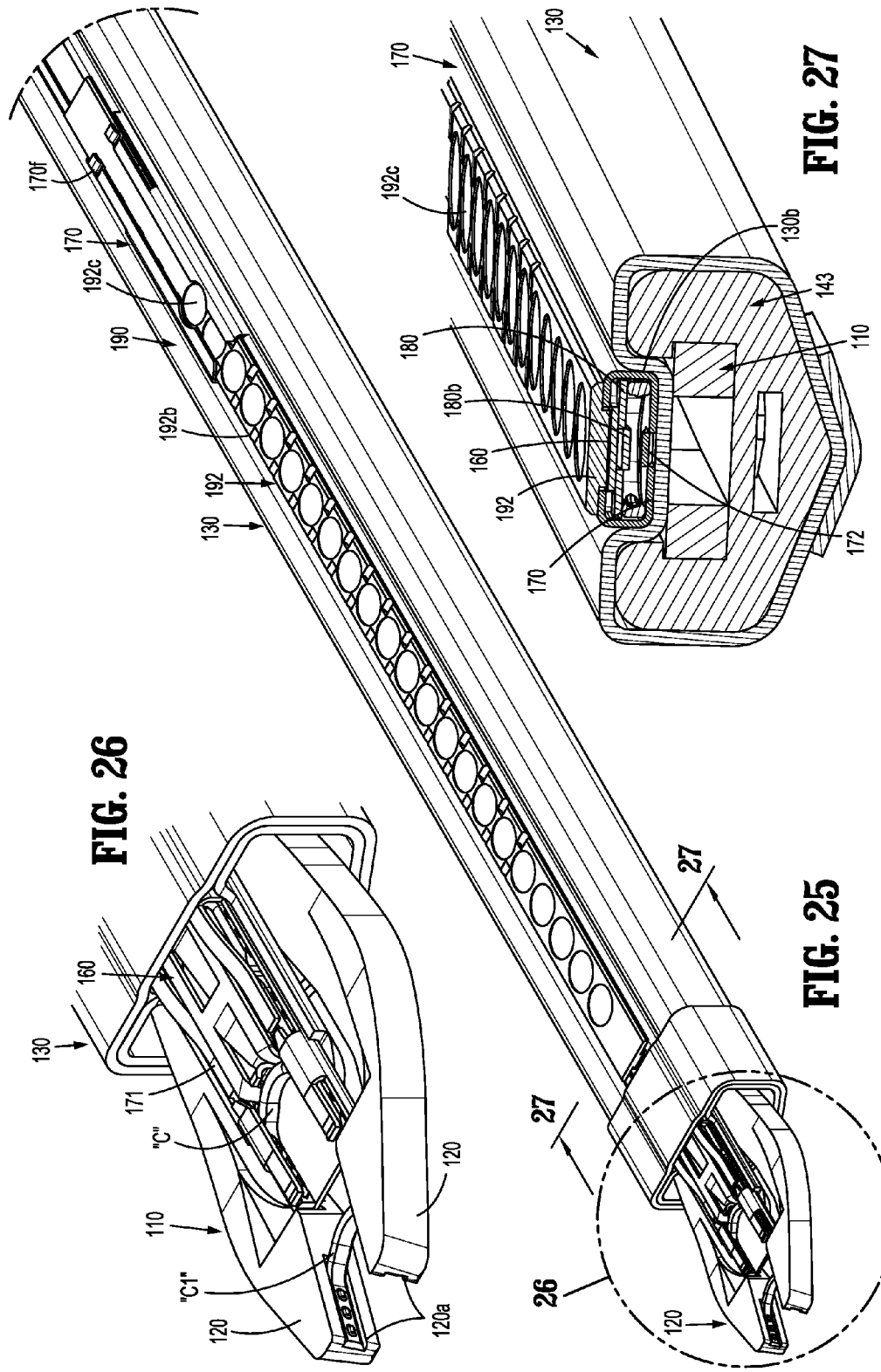

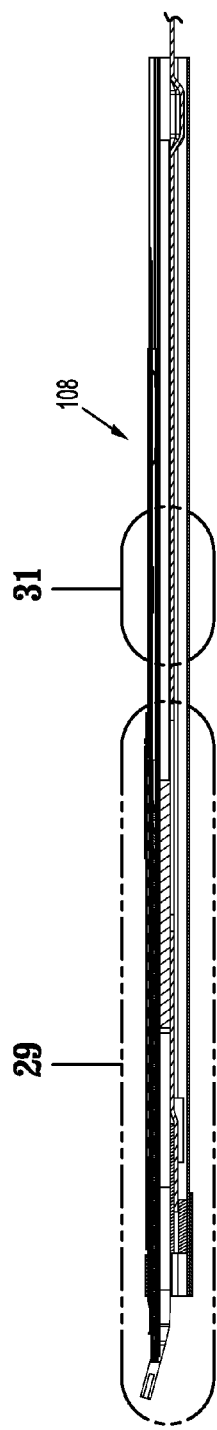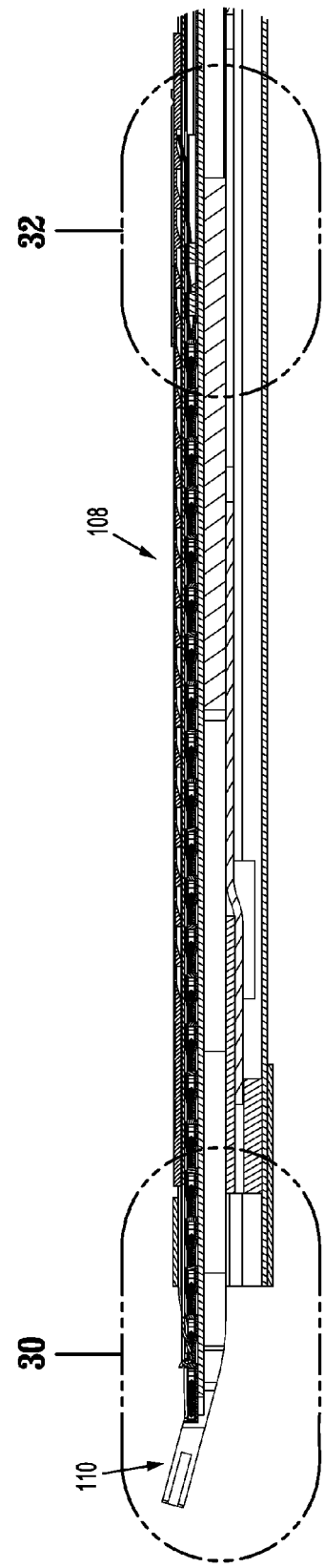
FIG. 28
FIG. 29

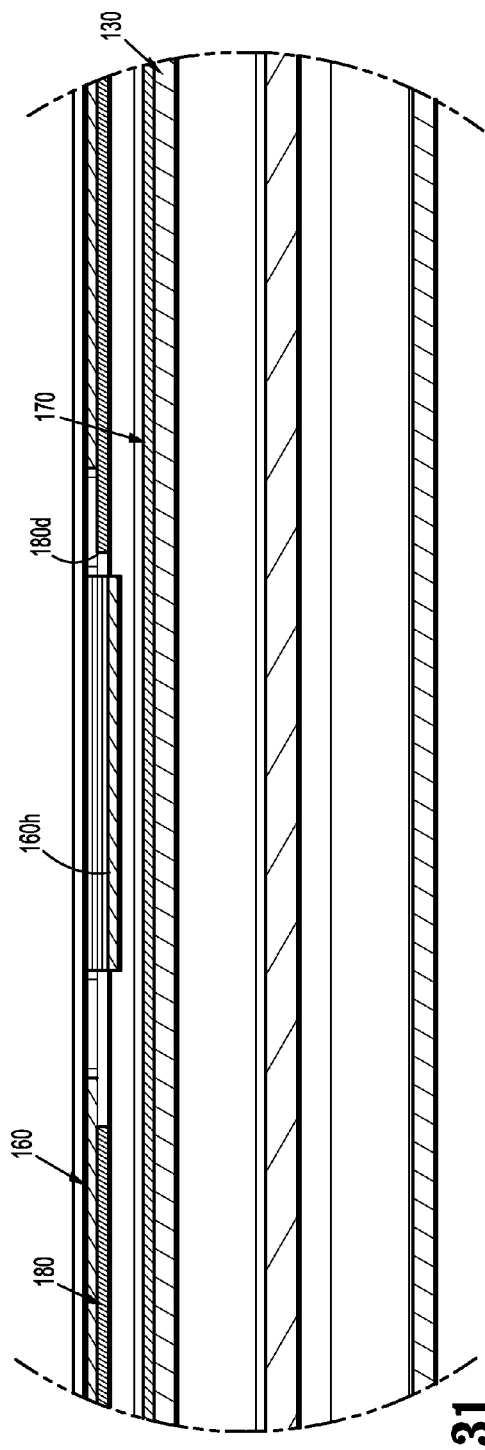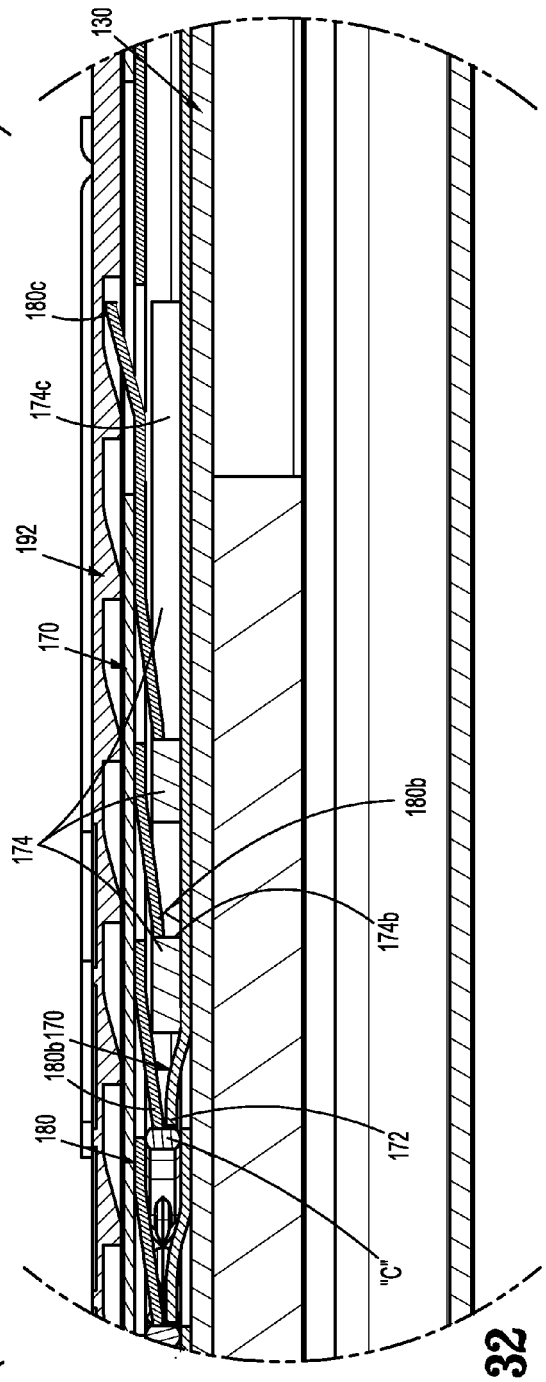

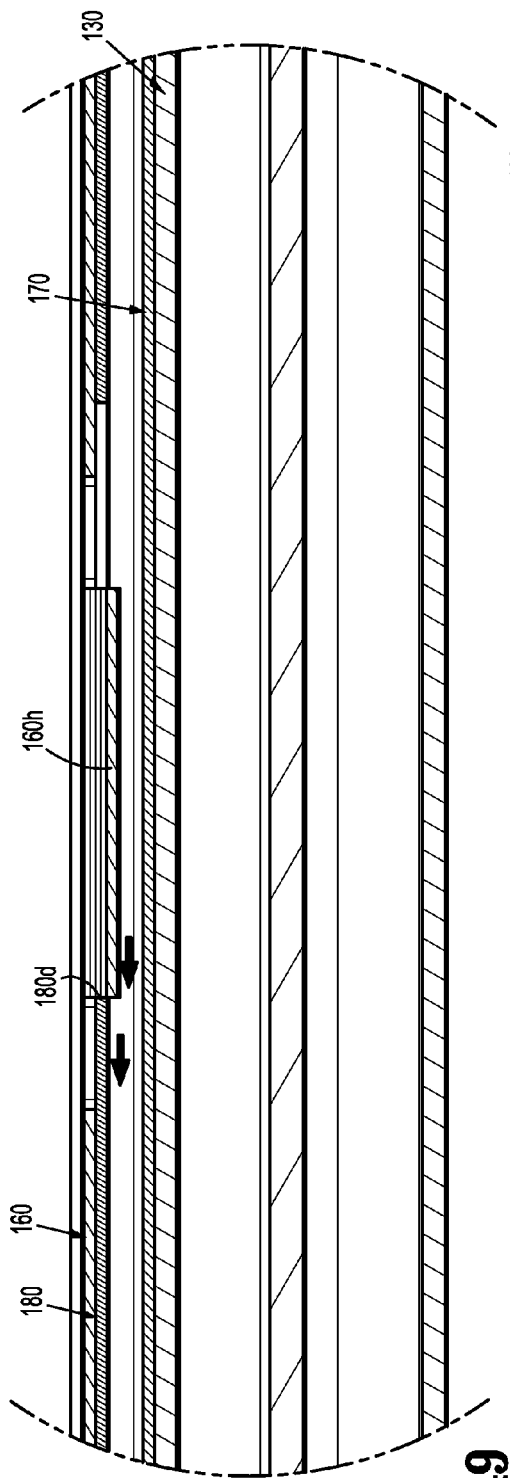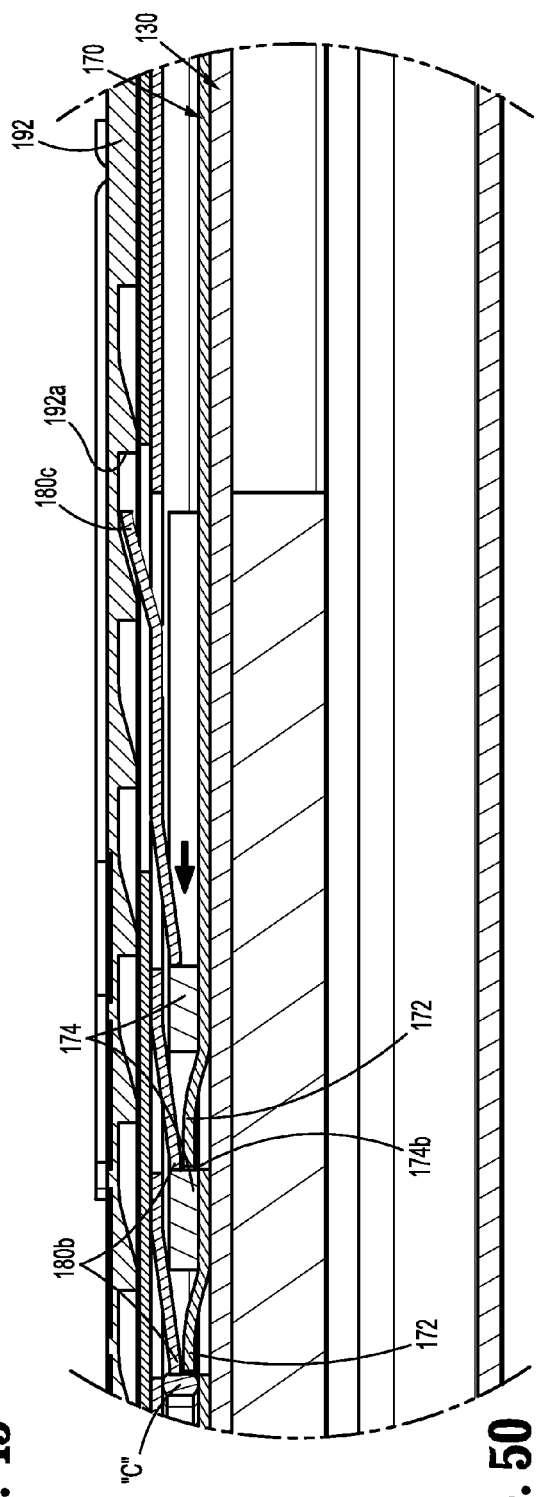

SURGICAL CLIP APPLIER WITH INTEGRATED CLIP COUNTER

CROSS REFERENCE TO RELATED APPLICATION

The present application claims the benefit of and priority to U.S. Provisional Application Ser. No. 61/581,116, filed on Dec. 29, 2011, the entire contents of which are incorporated herein by reference.

BACKGROUND

1. Technical Field

The present application relates to surgical instruments, and more particularly, to surgical clip appliers having a plurality of clips for applying the clips to body tissues and vessels during surgical procedures.

2. Discussion of Related Art

Surgical clip appliers are known in the art and have increased in popularity among surgeons by offering an alternative to conventional suturing of body tissues and vessels. Typical instruments are disclosed in U.S. Pat. No. 5,030,226 to Green et al. and U.S. Pat. No. 5,431,668 to Burbank III et al. These instruments generally provide a plurality of clips which are stored in the instrument and which are fed sequentially to the jaw mechanism at the distal end of the instrument upon opening and closing of the handles at the proximal end of the instrument. As the handles are closed, the jaws close to deform a clip positioned between the jaw members, and as the jaws are opened to release the deformed clip, a new clip is fed from the series to a position between the jaws. This process is repeated until all the clips in the series of clips have been used.

Many of these surgical clip appliers are relatively expensive to manufacture, purchase and/or operate. Thus, there is a desire by manufactures and end users to develop surgical clip appliers that are relatively inexpensive to manufacture, purchase and/or operate.

Additionally, many of these surgical clip appliers are operated by hand and the relative forces required to fire these surgical clip applier may be great.

Accordingly, a need exists for surgical clip appliers that are relatively economical to develop and manufacture, as well as requiring a relatively smaller firing force.

SUMMARY

The present application relates to surgical clip appliers having a plurality of clips for applying the clips to body tissues and vessels during surgical.

According to an aspect of the present disclosure, a surgical clip applier is provided and includes a housing; at least one handle pivotably connected to the housing; a channel assembly extending distally from the housing; a clip carrier disposed within the channel assembly defining a channel, the clip carrier including a plurality of distally oriented ramps extending into the clip channel; a plurality of clips slidably disposed within the channel of the clip carrier; a walking beam reciprocally disposed within the channel assembly and overlying the clip carrier, the walking beam being operatively connected to the at least one handle for reciprocal movement upon actuation of the at least one handle, the walking beam including a plurality of distally oriented ramps extending into the clip channel; and a clip follower slidably disposed within the channel of the clip carrier and disposed proximally of the plurality of clips, the clip follower being configured and adapted for selective engagement with the distally oriented ramps of the clip carrier and the distally oriented ramps of the walking beam, wherein the clip follower is configured and adapted to urge the plurality of clips, in a distal direction relative to the clip carrier, upon reciprocal movement of the walking beam.

The distally oriented ramps of the walking beam may be configured to selectively engage a first aperture defined in the clip follower and urge the clip follower distally upon distal movement of the walking beam, and the distally oriented ramps of the clip carrier may be configured to selectively engage a second aperture defined in the clip follower a stop proximal movement of the clip follower upon proximal movement of the walking beam.

The clip applier may further include a jaw assembly including a pair of jaws extending from an end of the channel assembly, opposite the housing. The jaw assembly may be adapted to accommodate a clip therein and may be operable to effect formation of a clip in response to movement of the at least one handle.

The clip applier may further include a clip pusher bar reciprocally positioned within at least one of the housing and the channel assembly. The pusher bar may have a first end operatively connected to the at least one handle and a second end defining a pusher. The pusher bar may be movable away from the pair of jaws as the at least one handle is actuated by an initial amount in order move the pusher behind a distal-most clip stored in the channel of the clip carrier. The pusher bar may be configured and adapted to move towards the jaws as the at least one handle is returned to a home position to move the distal-most clip between the jaws.

The clip pusher bar may be connected to the walking beam, wherein axial translation of the clip pusher bar results in concomitant axial translation of the walking beam.

The clip pusher bar and the walking beam may be configured and connected to one another such that a delay is provided between the axial translation of the clip pusher bar and the axial translation of the walking beam.

The clip applier may further include a drive linkage system configured to proximally move the pusher bar upon an actuation of the at least one handle, and configured to distally move the pusher bar upon a subsequent release of the at least one handle.

The clip applier may further include a drive channel translatably slidably disposed within at least one of the housing and the channel assembly. The drive channel may have a first end operatively connected to the at least one handle and a second end configured and dimensioned to selectively engage said pair of jaws to effectuate closure of the pair of jaws. The drive channel may be moved towards the jaw assembly as the at least one handle is moved in a first direction to move the second end of the drive channel against the pair of jaws to close the pair of jaws. The drive channel may be moved away from the jaw assembly as the at least one handle is moved in a second direction, opposite the first direction, to move the second end of the drive channel away from the jaw assembly to allow the pair of jaws to open.

The drive linkage system may include a distal linkage member having a first end pivotally connected to the pusher bar; and a crank member pivotally supported in the housing. The crank member may be substantially L-shaped and may have a first leg pivotally connected to a second end of the distal linkage member, and may have a second leg slidably connected in an actuate channel formed in the drive channel. In use, distal movement of the drive channel may cause the second leg of the crank member to slidably translate through the arcuate slot, thereby causing the crank member to rotate, thereby causing the first leg to rotate, thereby causing the distal linkage member to move proximally, and thereby causing the pusher bar to move proximally.

The clip follower may function as a lockout when the clip follower is advanced by the walking beam to a position between the pair of jaws. In use, when the clip follower is positioned between the pair of jaws, the clip follower may prevent the pair of jaws from completely closing and thus prevents the clip applier from completing a full closing stroke.

The clip applier may further include a clip counter plate slidably supported in the channel assembly, wherein the clip counter plate is configured and adapted to display a change in status of the clip applier upon each complete actuation of the at least one handle.

The clip counter plate may include a series of discrete indicia, wherein a selected one of the plurality of discrete indicia is discernable from the remainder of the discrete indicia. Each indicia of the plurality of discrete indicia may relate to a corresponding quantity of clips of the plurality of clips contained in the clip applier.

The clip counter plate may define a series of recesses formed in a first surface thereof, and wherein the walking beam may include a tab extending from a surface thereof and being dimensioned for receipt in each of the series of recesses formed in the clip counter plate. In use, as the walking beam moves, the tab may engage the clip counter plate to move the clip counter plate and change the selected one of the plurality of discrete indicia that is discernable from the remainder of the discrete indicia.

The discernable discrete indicia may be visible through the clip channel.

The clip applier may further comprise a clip counter plate slidably supported in the channel assembly. The clip counter plate may include indicia visible through the channel assembly, wherein the indicia corresponds to a quantity of clips loaded in the clip applier, wherein the clip counter plate is moved to decrement the indicia upon each firing of the clip applier resulting in the indicia corresponding to a quantity of clips of the plurality of clips remaining after the firing of the clip applier.

According to another aspect of the present disclosure, a surgical clip applier is provided and includes a housing; at least one handle pivotably connected to the housing; a channel assembly extending distally from the housing; a clip carrier disposed within the channel assembly defining a channel, the clip carrier including a plurality of distally oriented ramps extending into the clip channel; a plurality of clips slidably disposed within the channel of the clip carrier; a walking beam reciprocally disposed within the channel assembly and overlying the clip carrier, the walking beam being operatively connected to the at least one handle for reciprocal movement upon actuation of the at least one handle; and a clip pusher bar reciprocally positioned within at least one of the housing and the channel assembly, the pusher bar having a first end operatively connected to the at least one handle and a second end defining a pusher, the pusher bar being movable away from the pair of jaws as the at least one handle is actuated by an initial amount in order move the pusher behind a distal-most clip stored in the channel of the clip carrier, and said pusher bar being configured and adapted to move towards the jaws as the at least one handle is returned to a home position to move the distal-most clip between the jaws.

The clip applier may further include a clip follower slidably disposed within the channel of the clip carrier and disposed proximally of the plurality of clips, the clip follower being configured and adapted for selective engagement with the clip carrier and the walking beam, wherein the clip follower is configured and adapted to urge the plurality of clips, in a distal direction relative to the clip carrier, upon reciprocal movement of the walking beam.

The walking beam may include a plurality of distally oriented ramps extending into the clip channel, wherein the distally oriented ramps of the walking beam are configured to selectively engage a first aperture defined in the clip follower and urge the clip follower distally upon distal movement of the walking beam, and wherein the distally oriented ramps of the clip carrier are configured to selectively engage a second aperture defined in the clip follower a stop proximal movement of the clip follower upon proximal movement of the walking beam.

The clip applier may further include a jaw assembly including a pair of jaws extending from an end of the channel assembly, opposite the housing, the jaw assembly adapted to accommodate a clip therein and being operable to effect formation of a clip in response to movement of the at least one handle.

The clip pusher bar may be connected to the walking beam, wherein axial translation of the clip pusher bar results in concomitant axial translation of the walking beam. The clip pusher bar and the walking beam may be configured and connected to one another such that a delay is provided between the axial translation of the clip pusher bar and the axial translation of the walking beam.

The clip applier may further include a drive linkage system configured to proximally move the pusher bar upon an actuation of the at least one handle, and configured to distally move the pusher bar upon a subsequent release of the at least one handle.

The clip applier may further include a drive channel translatably slidably disposed within at least one of the housing and the channel assembly. The drive channel may have a first end operatively connected to the at least one handle and a second end configured and dimensioned to selectively engage said pair of jaws to effectuate closure of the pair of jaws. The drive channel may be moved towards the jaw assembly as the at least one handle is moved in a first direction to move the second end of the drive channel against the pair of jaws to close the pair of jaws. The drive channel may be moved away from the jaw assembly as the at least one handle is moved in a second direction, opposite the first direction, to move the second end of the drive channel away from the jaw assembly to allow the pair of jaws to open.

The drive linkage system may include a distal linkage member having a first end pivotally connected to the pusher bar; and a crank member pivotally supported in the housing. The crank member may be substantially L-shaped and may have a first leg pivotally connected to a second end of the distal linkage member, and may have a second leg slidably connected in an actuate channel formed in the drive channel. In use, distal movement of the drive channel may cause the second leg of the crank member to slidably translate through the arcuate slot, thereby causing the crank member to rotate, thereby causing the first leg to rotate, thereby causing the distal linkage member to move proximally, and thereby causing the pusher bar to move proximally.

The clip follower may function as a lockout when the clip follower is advanced by the walking beam to a position between the pair of jaws. In use, when the clip follower is positioned between the pair of jaws, the clip follower may prevent the pair of jaws from completely closing and thus may prevent the clip applier from completing a full closing stroke.

The clip applier may further include a clip counter plate slidably supported in the channel assembly, wherein the clip counter plate is configured and adapted to display a change in status of the clip applier upon each complete actuation of the at least one handle. The clip counter plate may include a series of discrete indicia, wherein a selected one of the plurality of discrete indicia is discernable from the remainder of the discrete indicia.

Each indicia of the plurality of discrete indicia may relate to a corresponding quantity of clips of the plurality of clips contained in the clip applier.

The clip counter plate may define a series of recesses formed in a first surface thereof, and wherein the walking beam may include a tab extending from a surface thereof and being dimensioned for receipt in each of the series of recesses formed in the clip counter plate. In use, as the walking beam moves, the tab may engage the clip counter plate to move the clip counter plate and change the selected one of the plurality of discrete indicia that is discernable from the remainder of the discrete indicia.

The discernable discrete indicia may be visible through the clip channel.

The clip applier may further include a clip counter plate slidably supported in the channel assembly. The clip counter plate may include indicia visible through the channel assembly, wherein the indicia corresponds to a quantity of clips loaded in the clip applier, wherein the clip counter plate is moved to decrement the indicia upon each firing of the clip applier resulting in the indicia corresponding to a quantity of clips of the plurality of clips remaining after the firing of the clip applier.

According to a further aspect of the present disclosure, a surgical clip applier is provided and includes a housing; at least one handle pivotably connected to the housing; a channel assembly extending distally from the housing; a clip carrier disposed within the channel assembly defining a channel, the clip carrier including a plurality of distally oriented ramps extending into the clip channel; a plurality of clips slidably disposed within the channel of the clip carrier; and a clip counter plate slidably supported in the channel assembly, wherein the clip counter plate is configured and adapted to display a change in status of the clip applier upon each complete actuation of the at least one handle.

The clip counter plate may include a series of discrete indicia, wherein a selected one of the plurality of discrete indicia is discernable from the remainder of the discrete indicia. Each indicia of the plurality of discrete indicia may relate to a corresponding quantity of clips of the plurality of clips contained in the clip applier.

The clip applier may further include a walking beam reciprocally disposed within the channel assembly and overlying the clip carrier, the walking beam being operatively connected to the at least one handle for reciprocal movement upon actuation of the at least one handle.

The clip counter plate may define a series of recesses formed in a first surface thereof, and wherein the walking beam may include a tab extending from a surface thereof and being dimensioned for receipt in each of the series of recesses formed in the clip counter plate. In use, as the walking beam moves, the tab may engage the clip counter plate to move the clip counter plate and change the selected one of the plurality of discrete indicia that is discernable from the remainder of the discrete indicia.

The discernable discrete indicia may be visible through the clip channel.

The clip applier may further include a clip pusher bar reciprocally positioned within at least one of the housing and the channel assembly. The pusher bar may have a first end operatively connected to the at least one handle and a second end may define a pusher. The pusher bar may be movable away from the pair of jaws as the at least one handle is actuated by an initial amount in order move the pusher behind a distal-most clip stored in the channel of the clip carrier. The pusher bar may be configured and adapted to move towards the jaws as the at least one handle is returned to a home position to move the distal-most clip between the jaws.

The clip applier may further include a clip follower slidably disposed within the channel of the clip carrier and may be disposed proximally of the plurality of clips. The clip follower may be configured and adapted for selective engagement with the clip carrier and the walking beam, wherein the clip follower may be configured and adapted to urge the plurality of clips, in a distal direction relative to the clip carrier, upon reciprocal movement of the walking beam.

The walking beam may include a plurality of distally oriented ramps extending into the clip channel, wherein the distally oriented ramps of the walking beam may be configured to selectively engage a first aperture defined in the clip follower and urge the clip follower distally upon distal movement of the walking beam, and wherein the distally oriented ramps of the clip carrier may be configured to selectively engage a second aperture defined in the clip follower a stop proximal movement of the clip follower upon proximal movement of the walking beam.

The clip applier may further comprise a jaw assembly including a pair of jaws extending from an end of the channel assembly, opposite the housing. The jaw assembly may be adapted to accommodate a clip therein and may be operable to effect formation of a clip in response to movement of the at least one handle.

The clip pusher bar may be connected to the walking beam, wherein axial translation of the clip pusher bar results in concomitant axial translation of the walking beam.

The clip pusher bar and the walking beam may be configured and connected to one another such that a delay is provided between the axial translation of the clip pusher bar and the axial translation of the walking beam.

The clip applier may further include a drive linkage system configured to proximally move the pusher bar upon an actuation of the at least one handle, and configured to distally move the pusher bar upon a subsequent release of the at least one handle.

The clip applier may further include a drive channel translatably slidably disposed within at least one of the housing and the channel assembly. The drive channel may have a first end operatively connected to the at least one handle and a second end configured and dimensioned to selectively engage said pair of jaws to effectuate closure of the pair of jaws. The drive channel may be moved towards the jaw assembly as the at least one handle is moved in a first direction to move the second end of the drive channel against the pair of jaws to close the pair of jaws. The drive channel may be moved away from the jaw assembly as the at least one handle is moved in a second direction, opposite the first direction, to move the second end of the drive channel away from the jaw assembly to allow the pair of jaws to open.

The drive linkage system may include a distal linkage member having a first end pivotally connected to the pusher bar; and a crank member pivotally supported in the housing. The crank member may be substantially L-shaped and may have a first leg pivotally connected to a second end of the distal linkage member, and may have a second leg slidably connected in an actuate channel formed in the drive channel. In use, distal movement of the drive channel may cause the second leg of the crank member to slidably translate through the arcuate slot, thereby causing the crank member to rotate, thereby causing the first leg to rotate, thereby causing the distal linkage member to move proximally, and thereby causing the pusher bar to move proximally.

The clip follower may function as a lockout when the clip follower is advanced by the walking beam to a position between the pair of jaws. In use, when the clip follower is positioned between the pair of jaws, the clip follower may prevent the pair of jaws from completely closing and thus prevents the clip applier from completing a full closing stroke.

BRIEF DESCRIPTION OF THE DRAWINGS

The present clip applier will be more fully appreciated as the same becomes better understood from the following detailed description when considered in connection with the following drawings, in which:

FIG. 3 is a top, perspective view of a channel assembly of the surgical clip applier of FIG. 1

FIG. 4 is a bottom, perspective view of the channel assembly of FIG. 3;

FIG. 6 is a top, perspective view of a pusher bar of the channel assembly of FIGS. 3 and 4;

FIG. 7 is a bottom, perspective view of the pusher bar of FIG. 6;

FIG. 8 is an enlarged view of the pusher bar of the indicated area of detail of FIG. 6;

FIG. 9 is a cross-sectional view of the pusher bar, as taken through 9-9 of FIG. 6;

FIG. 10 is a top, perspective view of a clip carrier of the channel assembly of FIGS. 3 and 4;

FIG. 11 is a bottom, perspective view of the clip carrier of FIG. 10;

FIG. 12 is an enlarged view of the clip carrier of the indicated area of detail of FIG. 10;

FIG. 13 is cross-sectional view of the clip carrier, as taken through 13-13 of FIG. 10;

FIG. 14 is a top, perspective view of a walking beam of the channel assembly of FIGS. 3 and 4;

FIG. 15 is a bottom, perspective view of the walking beam of FIG. 14;

FIG. 16 is an enlarged view of the walking beam of the indicated area of detail of FIG. 15;

FIG. 17 is an enlarged view of the walking beam of the indicated area of detail of FIG. 15;

FIG. 18 is a cross-sectional view of the walking beam, as taken through 18-18 of FIG. 14;

FIG. 19 is an enlarged view of the walking beam of the indicated area of detail of FIG. 18;

FIG. 20 is an enlarged view of the walking beam of the indicated area of detail of FIG. 18;

FIG. 21 is a top, perspective view of a clip counter plate of the channel assembly of FIGS. 3 and 4;

FIG. 22 is a bottom, perspective view of the clip counter plate of FIG. 21;

FIG. 23 is a cross-sectional view of the clip counter plate as taken through 23-23 of FIG. 21;

FIG. 24 is an enlarged view of the clip counter plate of the indicated area of detail of FIG. 23;

FIG. 25 is an enlarged, bottom, perspective view of the channel assembly of the indicated area of detail of FIG. 4;

FIG. 26 is an enlarged view of the channel assembly of the indicated area of detail of FIG. 25;

FIG. 27 is a cross-sectional view of the channel assembly as taken through 27-27 of FIG. 25;

FIG. 28 is a cross-sectional view of the channel assembly as taken through 28-28 of FIG. 4;

FIG. 29 is an enlarged view of the channel assembly of the indicated area of detail of FIG. 28;

FIG. 31 is an enlarged view of the channel assembly of the indicated area of detail of FIG. 28;

FIG. 32 is an enlarged view of the channel assembly of the indicated area of detail of FIG. 29;

FIG. 49 is an enlarged view of the indicated area 31 of FIG. 28, illustrating a distal movement of the pusher bar and the walking beam;

FIG. 50 is an enlarged, view of the indicated area 32 of FIG. 29, illustrating a distal movement of the pusher bar, the walking beam and the clip follower;

DETAILED DESCRIPTION OF EMBODIMENTS

Figure 1:
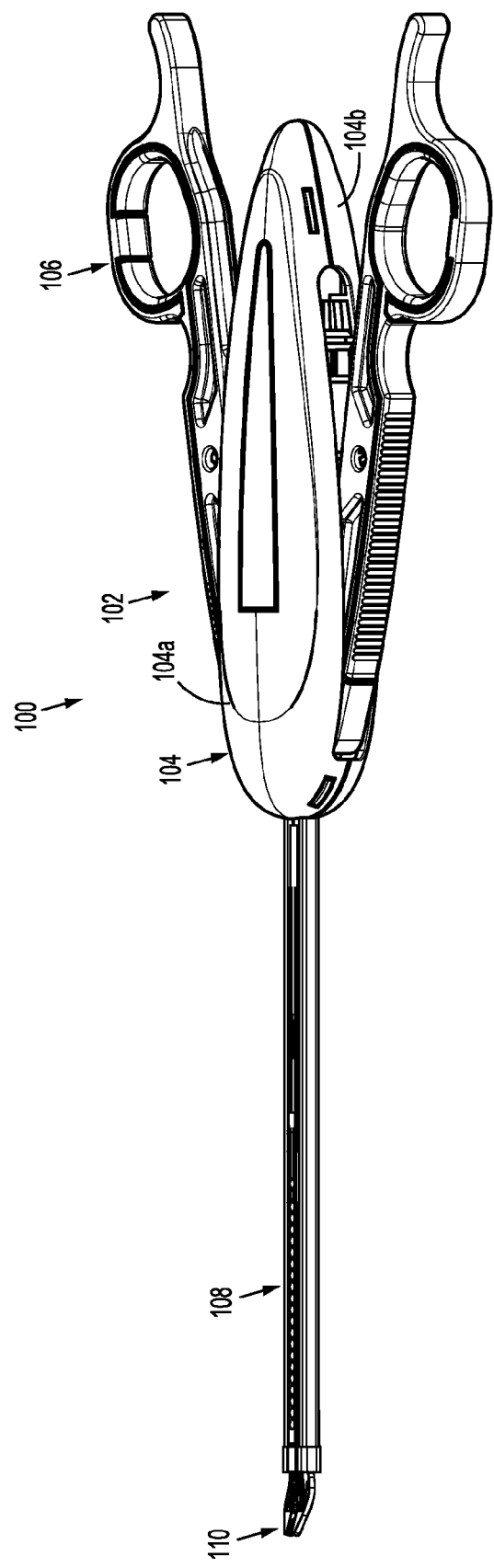
FIG. 1 is a perspective view of a surgical clip applier according to an embodiment of the present disclosure.

Embodiments of surgical clip appliers in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

FIGS. 1-4 illustrate a surgical clip applier in accordance with an embodiment of the present disclosure and is generally designated as 100.

Surgical clip applier 100 is a surgical instrument including a handle assembly 102 including a housing 104 having an upper housing half 104a and lower housing half 104b. Handle assembly 102 further includes a pair of handles 106 pivotally secured to housing 104 and extending outwardly therefrom. A channel assembly 108 is fixedly secured to housing 104 and extends outwardly therefrom, terminating in a jaw assembly 110.

Figure 2:
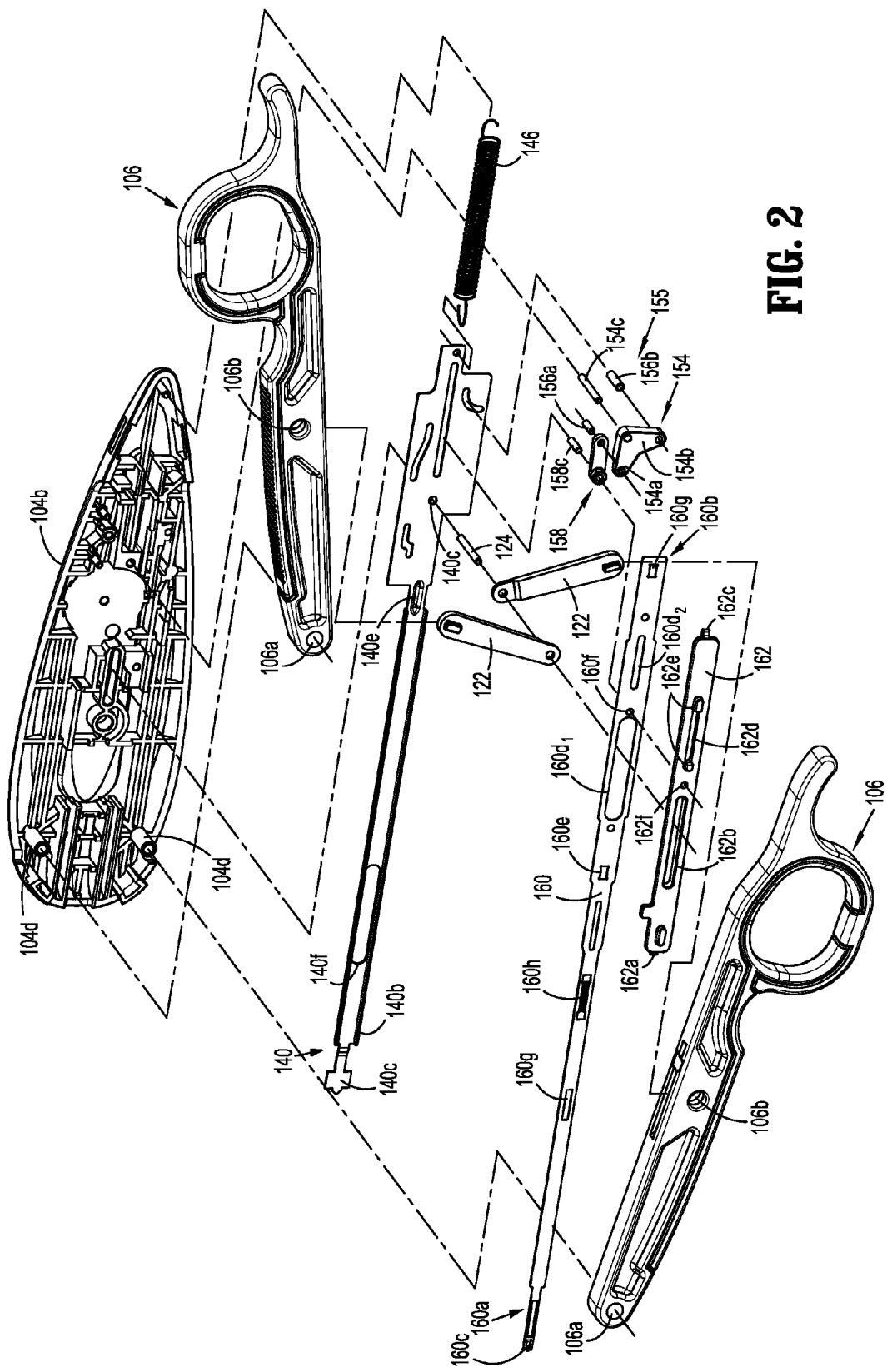
FIG. 2 is a perspective view, with parts separated, of a handle assembly of the surgical clip applier of FIG. 1.

As seen in FIGS. 1 and 2, housing halves 104a and 104h of clip applier 100 fit together by snap fit engagement with one another. Housing 104 is formed of a suitable plastic material.

As seen in FIG. 2, handles 106 are secured to housing 104 by handle pivot posts 104d extending from lower housing half 104b and into respective apertures 106a formed in handles 106. Handle assembly 102 includes a link member 122 pivotally connected to each handle 106 at a pivot point 106b formed in a respective handle 106. A distal end 122a of each link member 122 is pivotally connected to a pivot point 140a formed in a drive channel 140 via a drive pin 124. Each end of drive pin 124 is slidably received in an elongate channel 104e formed in a respective upper and lower housing half 104a, 104b. In use, as will be described in greater detail below, as handles 106 are squeezed, link members 122 push drive channel 140 distally via drive pin 124.

Channel assembly 108 includes a tubular body 130 having a proximal end retained in handle assembly 102, between upper and lower housing halves 104a, 104b. Tubular body 130 defines a lumen 130a therethrough and a longitudinally extending channel 130b formed in an outer surface thereof.

As seen in FIGS. 2 and 5-9, clip applier 100 includes a clip pusher bar 160 slidably disposed within handle housing 104 and channel assembly 108. Pusher bar 160 includes a distal end 160a defining a pusher 160c configured and adapted to selectively engage/move a distal-most clip "C1" stored in surgical clip applier 100. Pusher bar 160 further includes a proximal end 160b defining a first proximal window $160d_1$ and a second proximal window $160d_2$ therein. First proximal window $160d_1$ is configured for slidably receiving drive pin 124 therein and second proximal window $160d_2$ is configured for slidably receiving pivot pin 154c therein. Pusher bar 160 further defines a distal window 160e and a proximal window 160g therein for operative engagement with a stabilizer 162, as will be discussed in greater detail below, Pusher bar 160 further includes an aperture 160f configured to pivotally connect to a distal linkage member 158, as will described in greater detail below.

Handle assembly 102 of clip applier 100 further includes a stabilizer 162 configured to overlie and engage pusher bar 160. Stabilizer 162 includes a distal tab 162a configured to engage distal window 160e of pusher bar 160, elongate windows 162b and 162d defined therein at a location to substantially overlie and be in registration with respective proximal windows $160d_1$ and $160d_2$ formed in pusher bar 160. As seen in FIG. 2, stabilizer 162 further includes a plurality of tabs 162e extending from a top surface thereof, at a proximal and a distal location, which are configured and dimensioned for receipt in respective channels (not shown) formed in upper housing half 104a. Stabilizer 162 further includes an aperture 162f that overlies aperture 160f of pusher bar 160. Aperture 160f of pusher bar 160 and aperture 162f of stabilizer 162 are both configured to pivotally receive a pivot pin 158c extending through of distal linkage member 158.

As seen in FIG. 2, handle assembly 102 of clip applies 100 further includes a drive linkage system 155 in the form of a two-bar linkage system having distal linkage member 158 and a proximal crank member 154. Proximal crank member 154 that is pivotally supported in housing 104 via a pivot pin 154c. Proximal crank member 154 is substantially L-shaped including a first leg 154a pivotally connected to a proximal end of distal linkage member 158 via a first pivot pin 156a, and a second leg 154b pivotally and slidably connected to an arcuate slot 140g defined in drive channel 140 via a second pivot pin 156b. It is contemplated that first leg 154a of crank member 154 is oriented substantially orthogonal to second leg 154b of crank member 154.

As mentioned above, drive linkage system 155 includes distal linkage member 158 that interconnects proximal crank member 154 and pusher bar 160. A longitudinal axis "X1" is defined along an axis extending through drive pin 124, pivot pin 158c of distal linkage member 158, and pivot pin 154c. A side of longitudinal axis "X1," that includes second leg 154h of crank member 154, defines a first side, and the other side of longitudinal axis "X1", opposite the first side, defines a second side.

At an un-actuated condition of surgical clip applier 100, second leg 154b of crank member 154 is disposed on first side of longitudinal axis "X1", and first leg 154a of crank member 154 is disposed substantially along longitudinal axis "X1." As surgical clip applier 100 is actuated, first leg 154a of crank member 154 is disposed on second side of longitudinal axis "X1, as will be described in great detail below.

As seen in FIGS. 4-5 and 10-13, channel assembly 108 of clip applier 100 includes a clip carrier 170 disposed within channel 130b of tubular body 130 such that clip carrier 170 is interposed between tubular body 130 and pusher bar 160. Clip carrier 170 is generally a box-like structure having an upper wall 170a, a pair of side walls 170b and a lower wall 170c defining a channel 170d therethrough. Clip carrier 170 includes a plurality of spaced apart distally extending ramps 172 formed in lower wall 170c and extending longitudinally along a length thereof, wherein ramps 172 project toward the stack of clips "C". It is contemplated that a ramp 172 is provided for each surgical clip "C". Distally extending ramps 172 function to assist in maintaining the stack of clips "C" from moving proximally. Clip carrier 170 includes an elongate window 170e (as shown in FIG. 10) formed in upper wall 170a and extending longitudinally along an entire length thereof.

As seen in FIGS. 5, 25-30 and 32, a stack of surgical clips "C" is loaded and/or retained within channel 170d of clip carrier 170 in a manner so as to slide therewithin and/or therealong. Channel 170d is configured and dimensioned to slidably retain a stack or plurality of surgical clips "C" in tip-to-tail fashion therewithin.

As seen in FIGS. 12, 13 and 26, a distal end of clip carrier 170 includes a pair of spaced apart, resilient tangs 171. Tangs 171 are configured and adapted to selectively engage the legs and/or the backspan of a distal-most surgical clip "C1" of the stack of surgical clips "C" retained within carrier 170.

Figure 5:
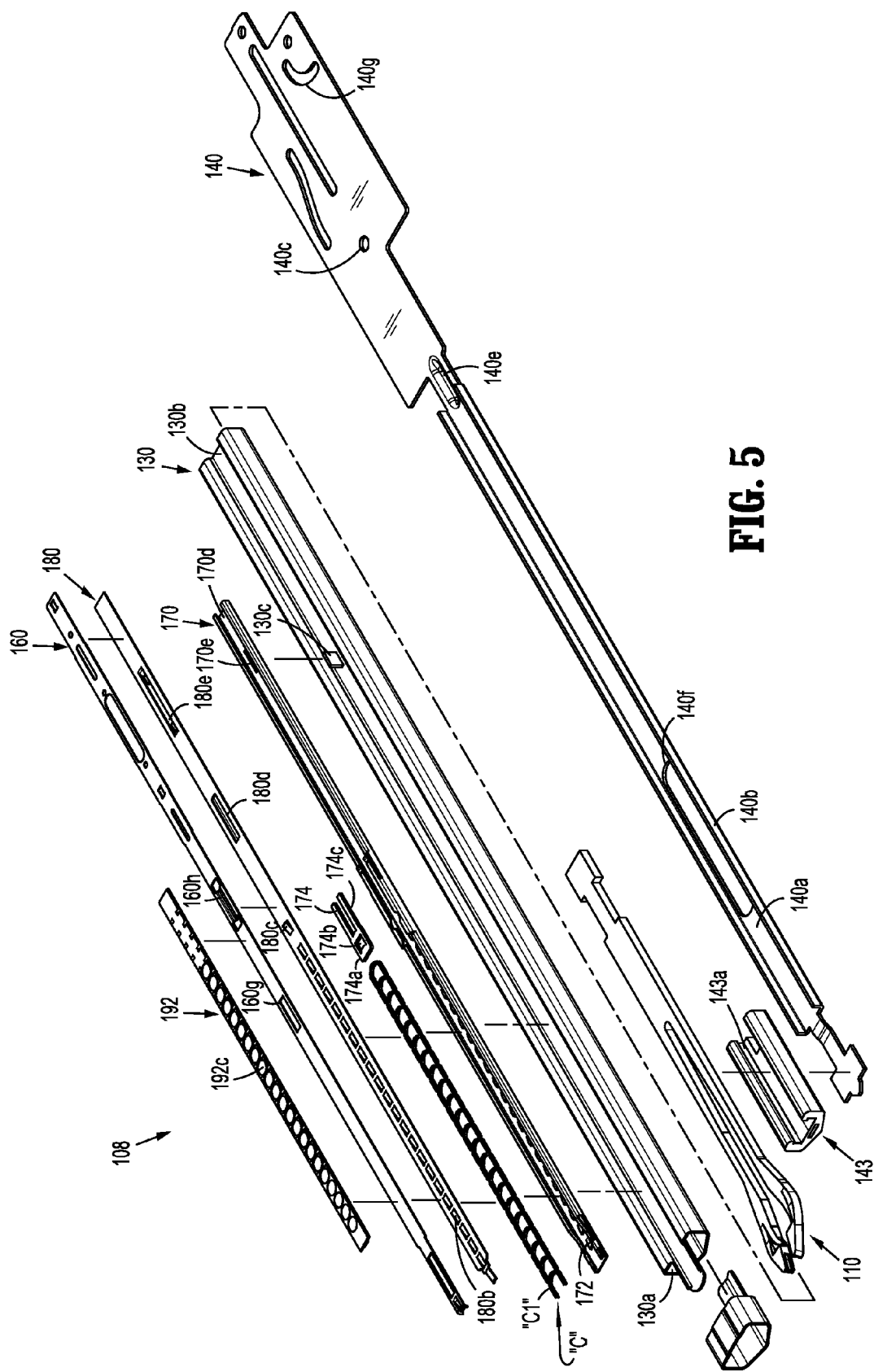
FIG. 5 is a perspective view, with parts separated, of the channel assembly of FIGS. 3 and 4.
Figure 30:
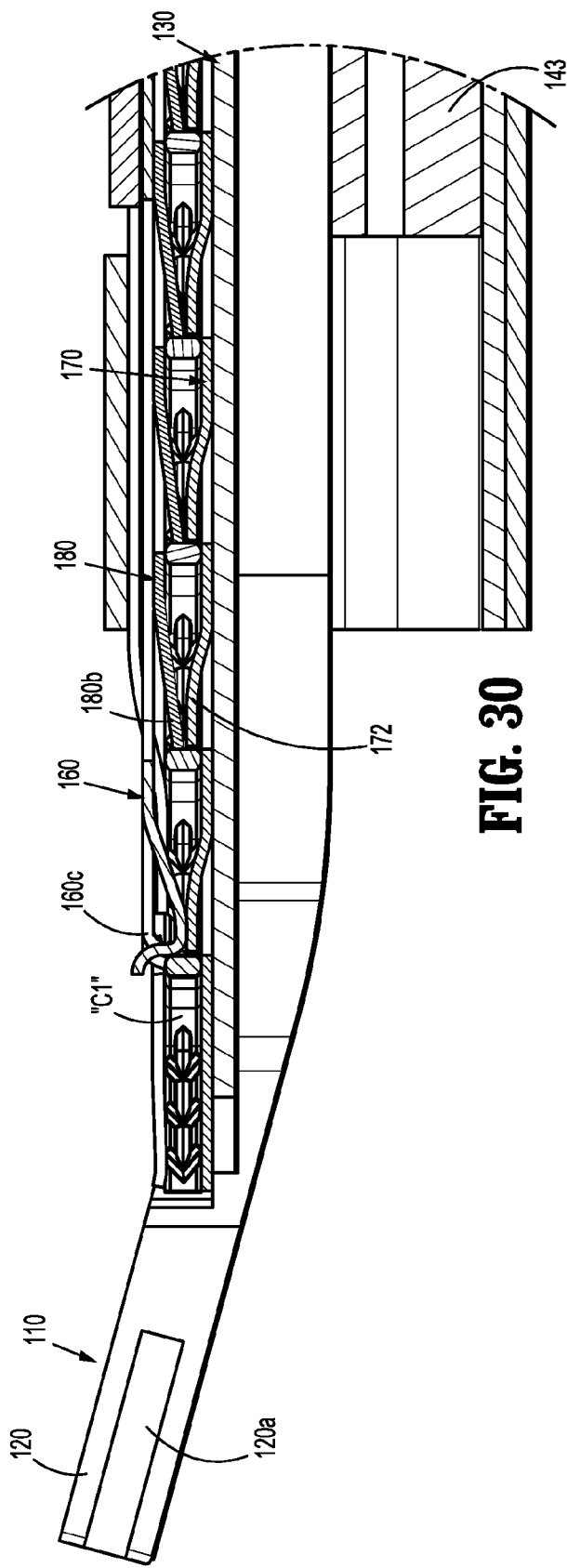
FIG. 30 is an enlarged view of the channel assembly of the indicated area of detail of FIG. 29.
Figure 33:
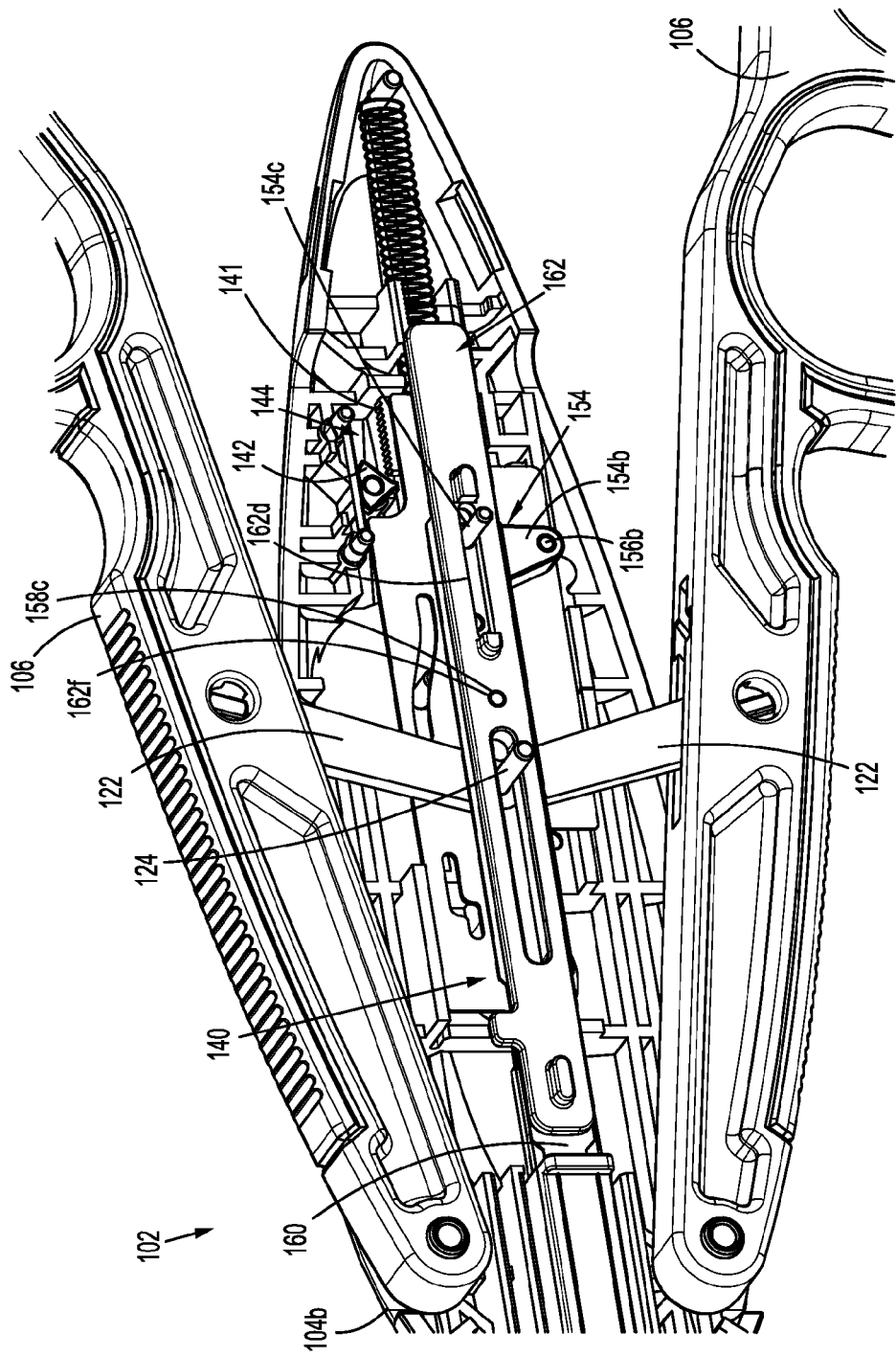
FIG. 33 is a perspective view of the handle assembly of the surgical clip applier of FIGS. 1 and 2, illustrated with an upper housing half removed therefrom.
Figure 34:
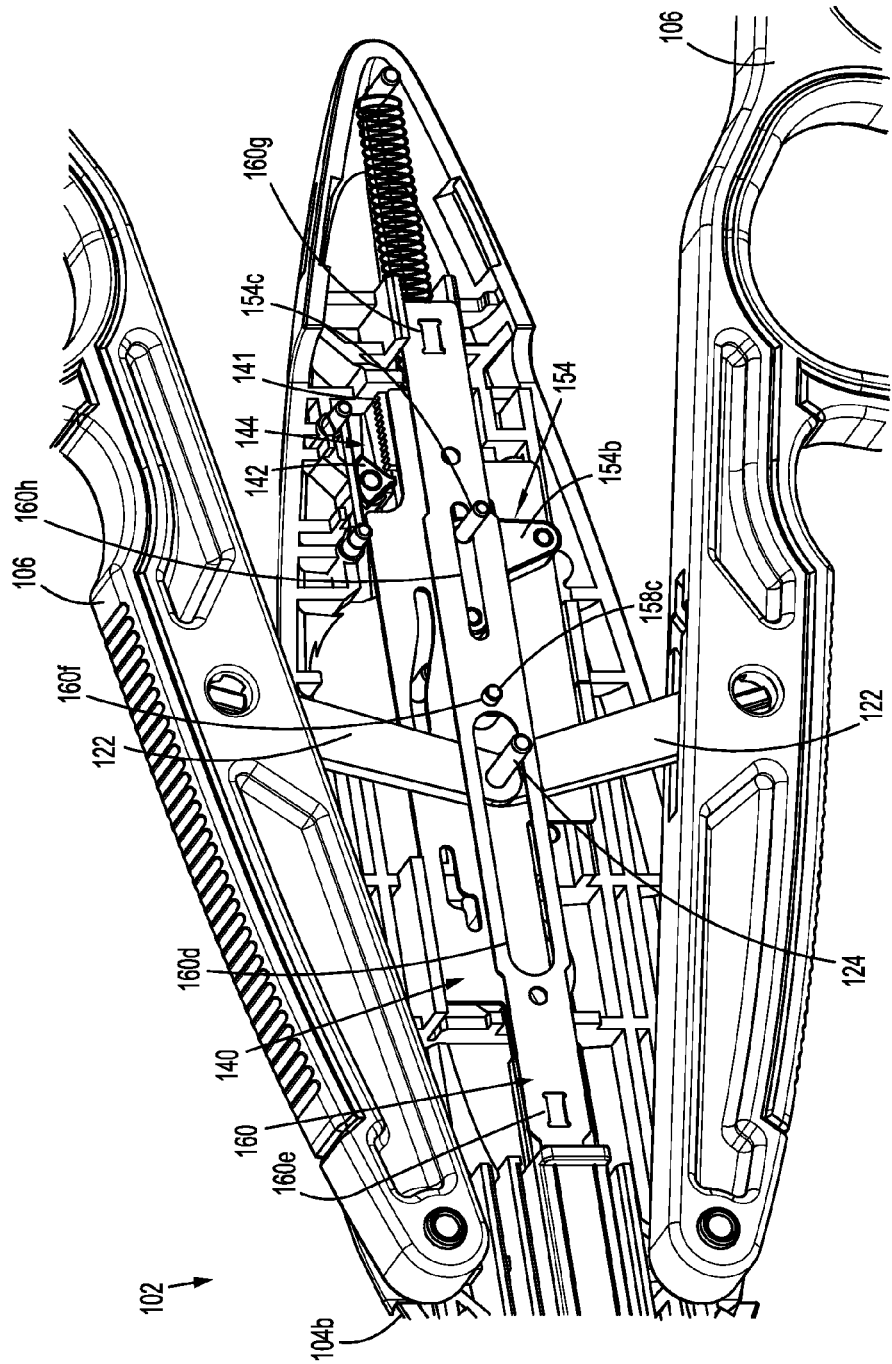
FIG. 34 is an enlarged view of the handle assembly of the surgical clip applier of FIGS. 1 and 2, illustrated with an upper housing half and a pusher stabilizer removed therefrom.
Figure 35:
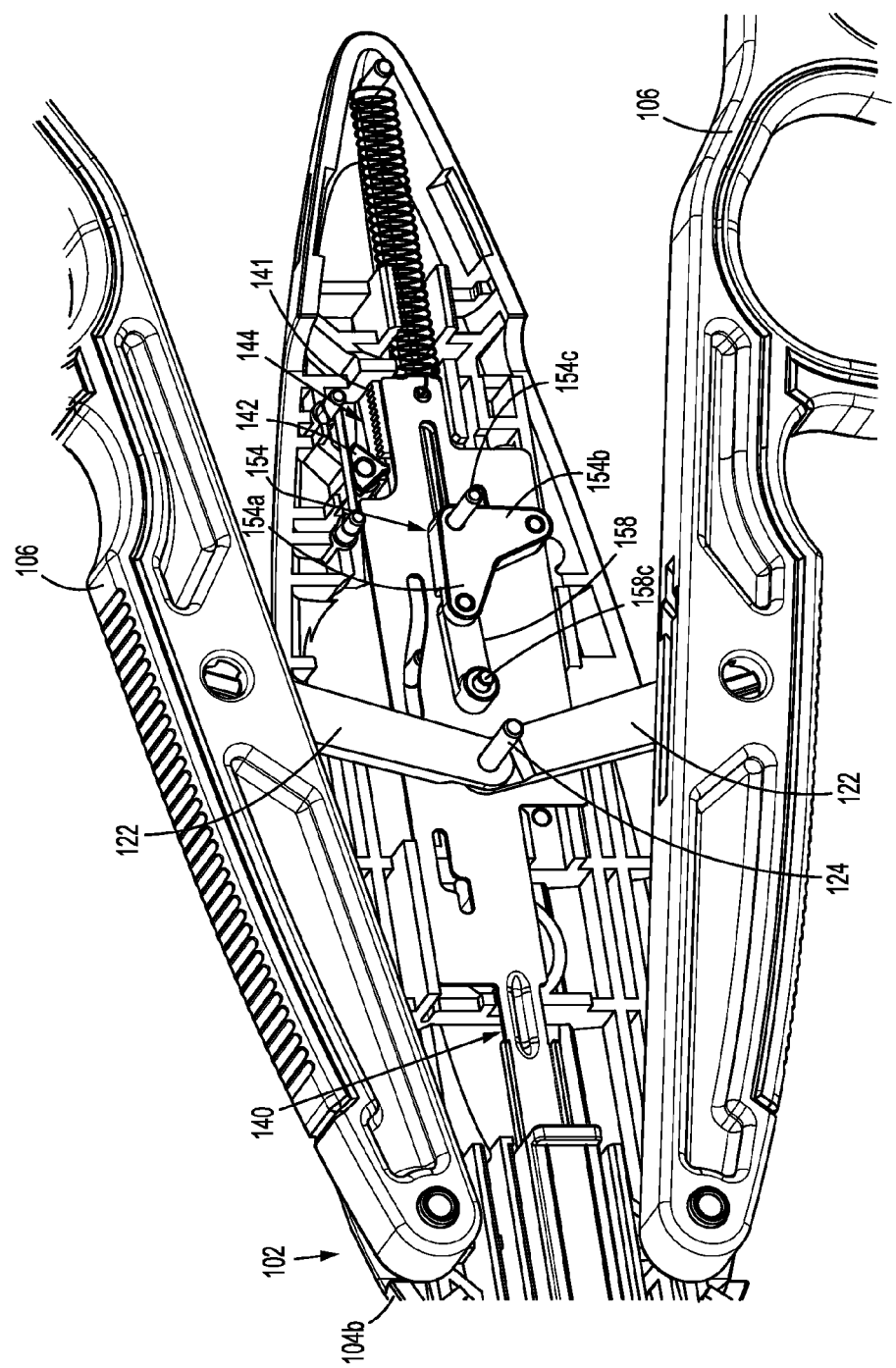
FIG. 35 is a top, perspective view of the handle assembly of the surgical clip applier of FIGS. 1 and 2, illustrated with the upper housing half, the pusher stabilizer and a pusher bar removed therefrom, shown in an un-actuated condition.
Figure 36:
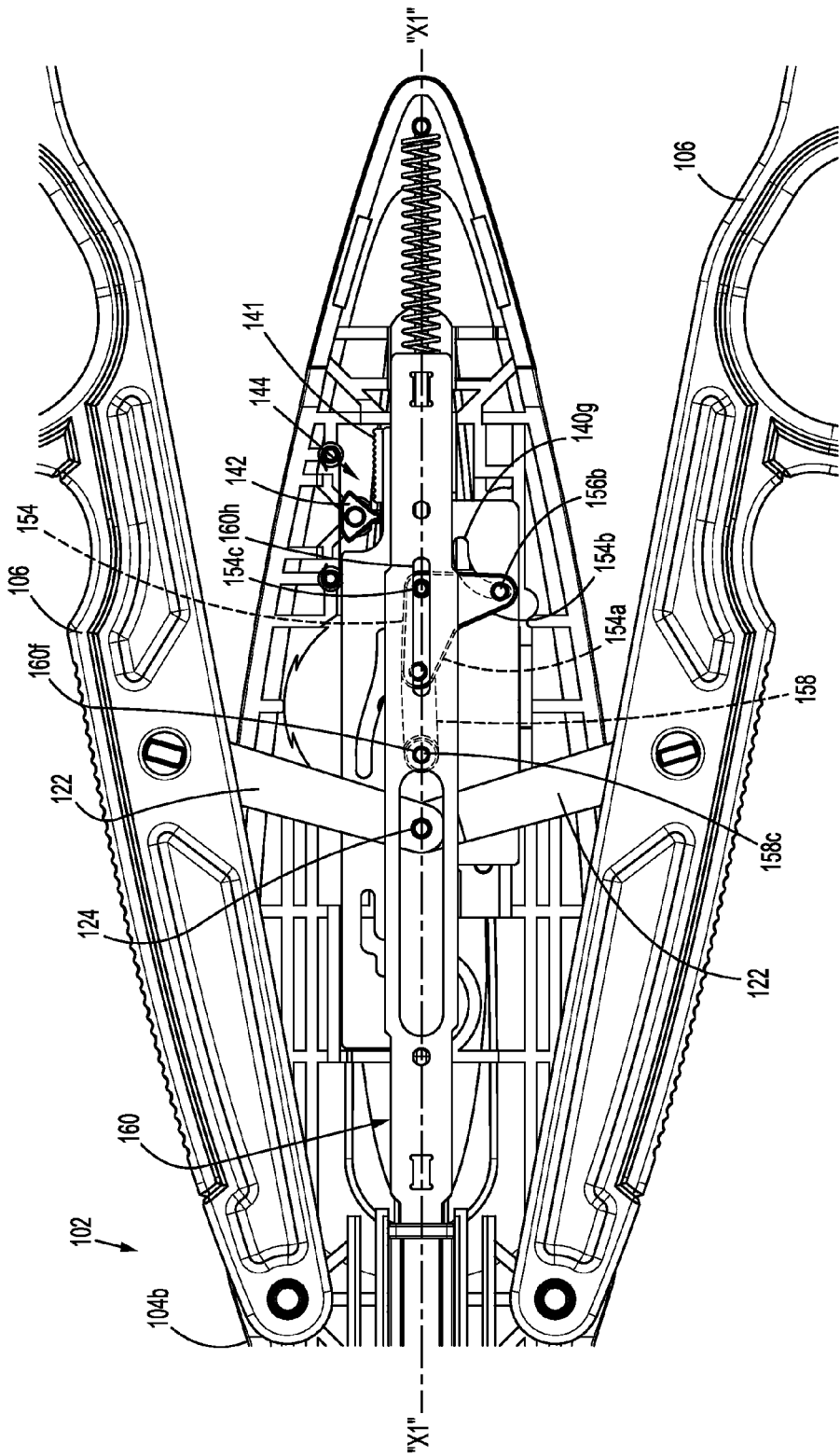
FIG. 36 is a top, plan view of the handle assembly of the surgical clip applier of FIGS. 1 and 2, with the upper housing half removed therefrom and shown in an un-actuated condition.
Figure 37:
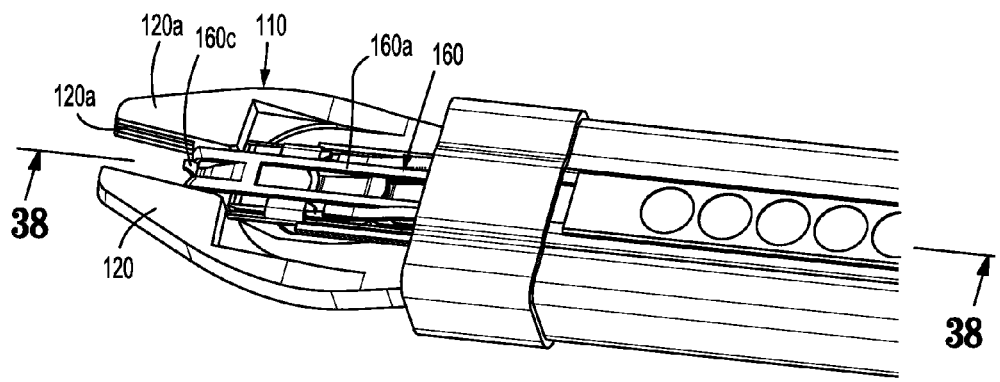
FIG. 37 is a top, perspective view of a distal end of the channel assembly of the surgical clip applier of FIGS. 1 and 2, illustrating the pusher bar, a drive channel and a walking beam in an un-actuated condition.
Figure 38:
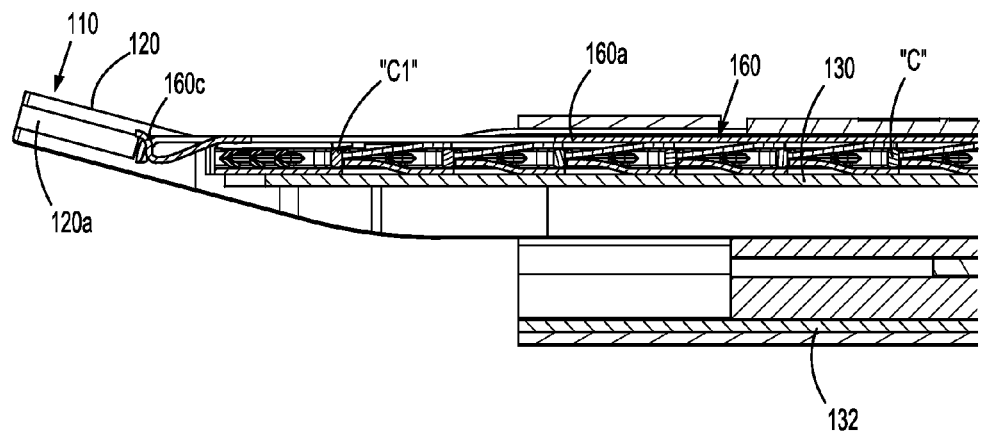
FIG. 38 is a cross-sectional view of the distal end of the channel assembly of the surgical clip applier, as taken through 38-38 of FIG. 37.

As seen in FIG. 5, channel assembly 108 of clip applier 100 further includes a clip follower 174 slidably disposed within channel 170d of clip carrier 170. As will be discussed in greater detail below, clip follower 174 is positioned behind the stack of surgical clips "C" and is provided to urge the stack of clips "C" forward during an actuation of clip applier 100. As will also be described in greater detail below, clip follower 174 is actuated by the reciprocating forward and backward motion of a walking beam 180. Clip follower 174 functions as a lock-out following the firing of the final surgical clip of the stack of clips "C", as will be described in greater detail below.

As seen in FIG. 5, clip follower 174 includes body portion 174a defining a plane, a distal window 174b defined in body portion 174a, and at least one leg 174c extending proximally from body portion 174a, so as to act as a stabilizing feature for clip follower 174. Distal window 174b is configured and dimensioned to selectively receive ramps 172 projecting distally from upper wall 170a of clip carrier 170. In use, engagement of ramps 172 of clip carrier 170 against a distal wall of body portion 174a, as defined by distal window 174b of clip follower 174, prevents clip follower 174 from traveling or moving in a proximal direction.

Distal window 174b of clip follower 174 is also configured and dimensioned to selectively receive ramps 180b projecting and extending distally from a walking beam 180. In use, engagement of ramps 180b of walking beam 180 against a distal wall of body portion 174a, as defined by distal window 174b of clip follower 174, drives clip follower 174 in a distal direction as walking beam 180 is moved in a distal direction.

As seen in FIGS. 3-5, 25 and 26, channel assembly 108 of clip applier 100 includes a jaw assembly 110 having a pair of jaws 120 mounted on or at a distal end of channel assembly 108 and actuatable by handles 106 of handle assembly 102. Jaws 120 are formed of a suitable biocompatible material such as, for example, stainless steel or titanium.

Jaws 120 are mounted in a distal end of drive channel 140 via one or more rivets or the like extending through reciprocation limiting slot 140f of drive channel 140 such that jaws 120 are longitudinally stationary relative to outer channel 132 and drive channel 140. As seen in FIG. 26, jaws 120 define a channel 120a therebetween for receipt of a surgical clip "C1" therein.

As seen in FIGS. 5, 14-20 and 27-32, channel assembly 108 of clip applier 100 further includes a walking beam 180 slidably disposed within handle assembly 102 and channel assembly 108. In particular, walking beam 180 is positioned or disposed within channel 170d of clip carrier 170 and overlies the stack of clips "C". Walking beam 180 includes a substantially tapered distal end or nose 180a. Walking beam 180 defines a plurality of spaced apart distally extending ramps 180b formed therein and extending longitudinally along a length thereof, and projecting towards the stack of clips "C". It is contemplated that a ramp 180b is provided for each surgical clip "C". Distally extending ramps 180b function to move the stack of clips "C" distally when the walking beam 180 is moved distally and to assist in maintaining the stack of clips "C" from moving proximally.

Walking beam 180 further includes a proximally extending ramp 180c, disposed proximally of ramps 180b, and projecting along an opposite side of walking beam 180. Ramp 180c of walking beam 180 extends through a window 160g formed in pusher bar 160, so as to engage recesses 192a (see FIGS. 22 and 24) defined in a surface of clip counter plate 192, as will be described in greater detail below.

Walking beam 180 also includes a first slot 180d formed therein for receiving a rib or tab 160h projecting from pusher bar 160. In accordance with the present disclosure, first slot 180d of walking beam 180 has an axial length that is shorter than an axial length of tab 160h of pusher bar 160. In this manner, as pusher bar 160 is reciprocated, as described hereinbelow, walking beam 180 is also reciprocated therewith following a degree of lost motion until tab 160h of pusher bar 160 engages a distal end or a proximal end of first slot 180d of walking beam 180.

Walking beam 180 further defines a second slot 180e therein which is configured and dimensioned to receive a stop post 130c extending from tubular body 130. Stop post 130c extends through clip carrier 170 and into second slot 180e of walking beam 180. In use, as walking beam 180 is reciprocated axially in a distal or proximal direction, stop post 130c engages a distal end or a proximal end of second slot 180e of walking beam 180 to limit a distance of axial travel of walking beam 180.

As seen in FIGS. 5 and 21-27, clip applies 100 further includes a counter mechanism 190 supported in channel assembly 108. Counter mechanism 190 includes a clip counter plate 192 slidably supported atop pusher bar 160. Counter plate 192 is selectively held in position relative to clip carrier 170 by resilient fingers 170f engaging notches 192b formed in a surface of counter plate 192. In use, as walking beam 180 is moved proximally due to a proximal movement of pusher bar 160 and the engagement of rib 160h of pusher bar 160 in window 180d of walking beam 180, clip counter plate 192 is moved proximally due to the engagement of proximally extending ramp 180c of walking beam 180 against notches 192a formed in the lower surface of clip counter plate 192. Clip counter plate 192 is moved proximally until resilient fingers 170f of clip carrier 170 engage the next distal-most notches 192b of clip counter plate 192 to thereby hold the axial position of clip counter plate 192 relative to clip carrier 170. Then, as walking beam 180 is moved distally due to a distal movement of pusher bar 160 and the engagement of rib 160h of pusher bar 160 in window 180d of walking beam 180, clip counter plate 192 continues to be held in position due to the engagement of resilient fingers 170f of clip carrier 170 in the next distal-most notches 192b of clip counter plate 192.

As clip counter plate 192 is moved in a proximal direction, an index or indicia 192c disposed on a surface thereof is moved into registration with a window or indicator formed in a cover overlying and fixed to channel 130b of tubular body 130. In operation, as clip counter plate 192 is moved in a proximal direction, indicia 192c, in the form of numerals or the like, are decremented to indicate the total number of clips "C" remaining in surgical clip applier 100.

As seen in FIGS. 2-5, clip applier 100 includes a drive channel 140 reciprocally supported in and extending between housing 104 of handle assembly 102 and channel assembly 108. A proximal end of drive channel 140 is supported between upper and lower housing halves 104a, 104b of housing 104 and a distal end of drive channel 140 is supported between cartridge cover 130 and outer channel 132 of channel assembly 108, at a location below walking beam 180.

A distal end of drive channel 140 is a substantially U-shaped channel including a pair of spaced apart side walls 140b extending from a backspan 140c thereof, in a direction away from outer channel 132 and toward cartridge cover 130. Drive channel 140 further defines a drive pin recess 140a formed in backspan 140c for pivotally receiving drive pin 124 therethrough. Drive channel 140 further defines a rib 140e projecting from backspan 140c at a location distal of drive pin recess 140a. Drive channel 140 also defines a reciprocation limiting slot 140f formed in backspan 140c at a location distal of rib 140e. Additionally, drive channel 140 defines an arcuate slot 140g formed therein and being configured and dimensioned to slidably receive second pivot pin 156b that is pivotably connected to second leg 154b of crank member 154.

As seen in FIGS. 5 and 27, clip applier 100 includes a drive channel cam block 143 secured to drive channel 140. In particular, cam block 143 is secured to a distal end of drive channel 140 and includes defines a camming channel 143a defined by a pair of side walls configured and dimensioned to lay outward of jaws 120. Cam block 143 is secured to drive channel 140 such that cam block 143 reciprocates with the movement of drive channel 140.

It is contemplated that clip applier 100 may further include an audible/tactile indicator (not shown) connected to drive channel 140 via drive pin 124. The indicator includes a resilient finger and a pair of bosses. In use, as clip applier 100 is actuated and drive channel 140 is reciprocated, a first resilient finger of indicator interacts with corresponding complementary structure or ledge (not shown) provided in clip applier 100 to create an audible and/or a tactile feedback to the user. The bosses of indicator ride within a channel formed in upper housing half 104a and provide support to the indicator to prevent the indicator from rotating.

As seen in FIG. 2, handle assembly 102 of clip applier 100 further includes a biasing member 146, in the form of a tension spring, operatively secured to and between a proximal end of drive channel 140 and housing 104, tending to maintain drive channel 140 in a retracted or proximal-most position. Biasing member 146 functions to retract or facilitate retraction of drive channel 140 following formation of a clip "C" positioned between jaws 120.

As seen in FIGS. 33-36, handle assembly 102 of clip applier 100 includes a ratchet member 141 secured to a proximal end of drive channel 140, via drive pin 124, so as to be movable together with drive channel 140. Ratchet rack member 141 is configured and adapted to engage with a ratchet pawl 142 supported in housing 104. Rack member 141 and ratchet pawl 142 define a ratchet mechanism 144. In use, as drive channel 140 is moved axially, rack member 141 is also moved. Rack member 141 defines a series of rack teeth having a length which allows pawl 142 to reverse and advance back over rack member 141 when rack member 141 changes between proximal and distal movement as drive channel 140 reaches a proximal-most or distal-most position.

Pawl 142 is pivotally connected to lower housing half 104b by a pawl pin at a location wherein pawl 142 is in substantial operative engagement with rack member 141. Pawl 142 is engageable with rack member 141 to restrict longitudinal movement of rack member 141 and, in turn, drive channel 140. Ratchet mechanism 144 further includes a pawl spring configured and positioned to bias pawl 142 into operative engagement with rack member 141. Pawl spring functions to maintain the teeth of pawl 142 in engagement with the teeth 141a of rack member 141, as well as to maintain pawl 142 in a rotated or canted position.

With reference to FIGS. 1-32 and 33-55, the operation of clip applier 100 is provided. Prior to any initial squeezing of handles 106 of clip applier 100, as seen in FIGS. 33-38, the internal components of the clip applier 100 are in a so-called "home" or "starting" or un-actuated position. More particularly, in the "home" position, the drive pin 124 is located at a proximal-most position, pawl 142 is located distal of rack 140d of drive channel 140, second finger 179c of pivot arm 179 is located at a distal-most position in the distal portion of window 140g of drive channel 140 such that walking beam 180 is located at a distal-most position, no clips "C" are positioned within jaws 120, and pusher 160a of pusher bar 160 is disposed distal of clips "C". Also, with drive pin 124 at a proximal-most position, pusher bar 160 is disposed at a distal-most position and drive channel 140 is disposed at a proximal-most position.

Prior to an initial squeezing of handles 106 of clip applier 100, with walking beam 180 located at a distal-most position, distal end 180a thereof is interposed between jaws 120. Also prior to the initial squeeze of handles 106 of clip applier 100, there are no clips "C" present within jaws 120. A clip "C" is first loaded into jaws 120 during the initial squeezing of handles 106 in order to prime clip applier 100 with a first clip "C1" into jaws 120.

As seen in FIGS. 39-47, during/following a complete initial squeeze of handles 106 (i.e., a working stroke), to prime surgical clip applier 100, distal ends 122a of link members 122 are moved distally relative to housing 104. As distal ends 122a of link members 122 are moved distally, drive pin 124 is moved distally thereby transmitting distal axial movement to drive channel 140.

Figure 39:
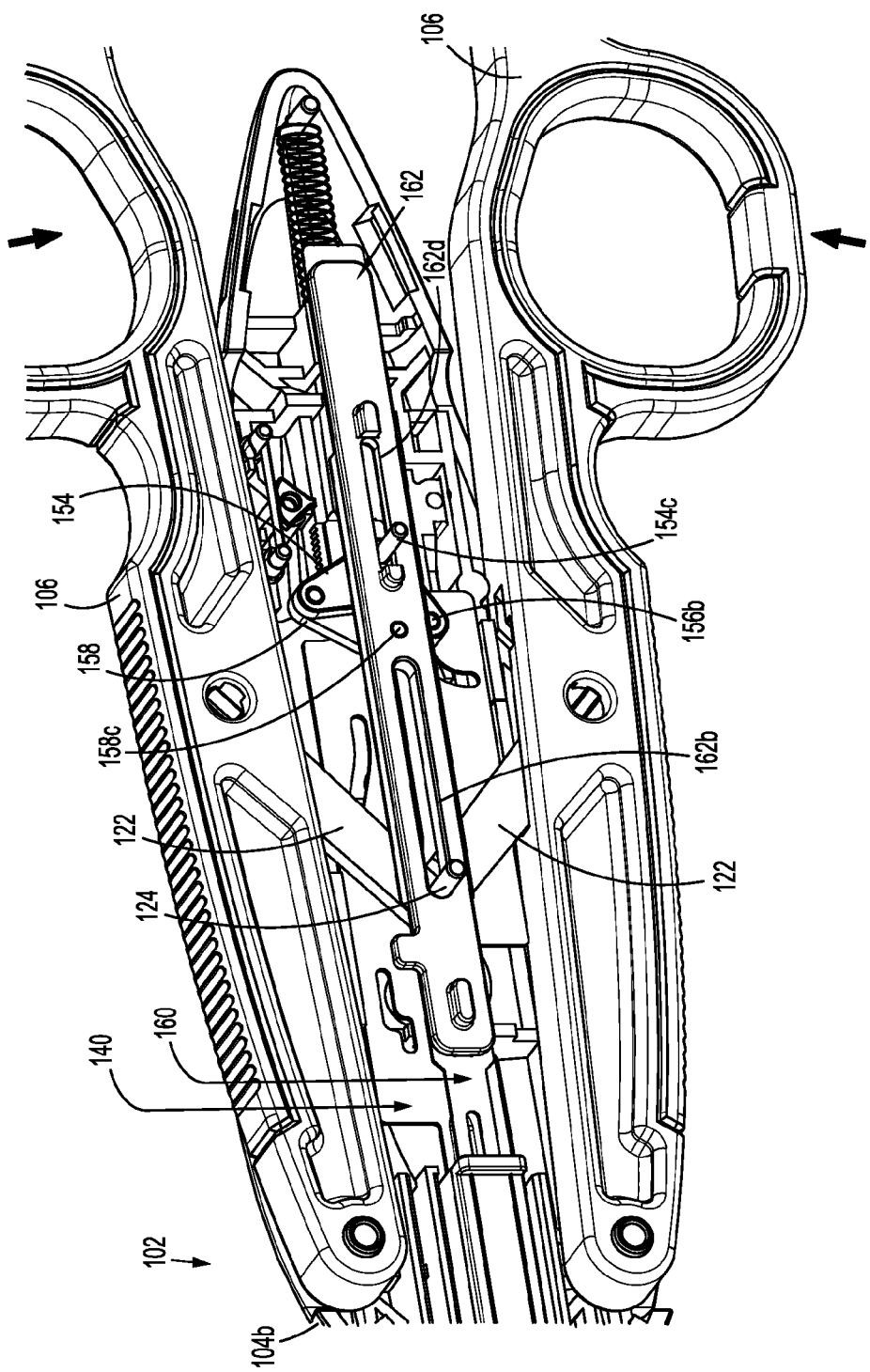
FIG. 39 is a top, perspective view of the handle assembly of the surgical clip applier of FIGS. 1 and 2, with the upper housing half removed therefrom and shown following a first complete actuation.
Figure 40:
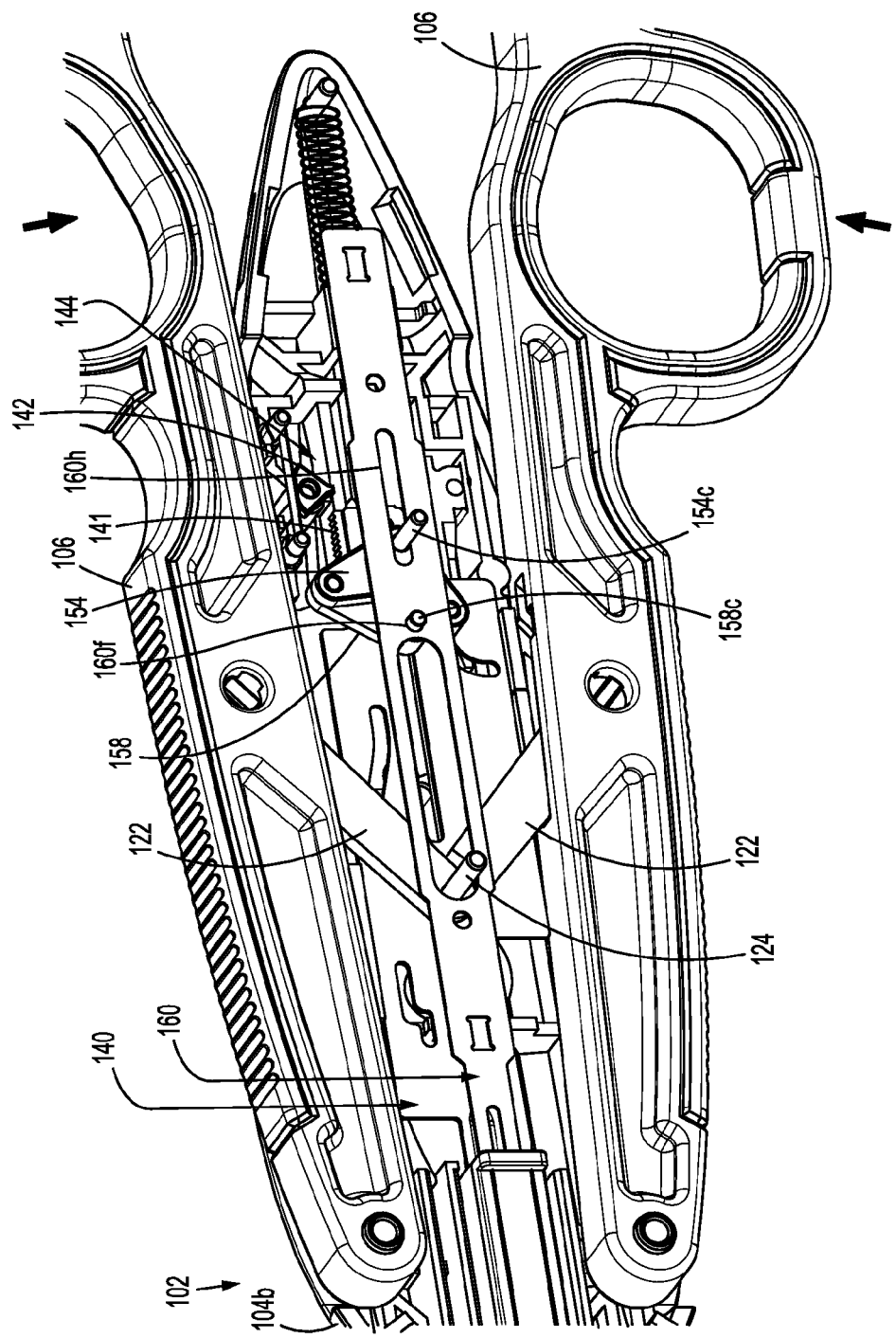
FIG. 40 is a top, perspective view of the handle assembly of the surgical clip applier of FIGS. 1 and 2, with the upper housing half and the pusher stabilizer removed therefrom and shown following the first complete actuation.
Figure 41:
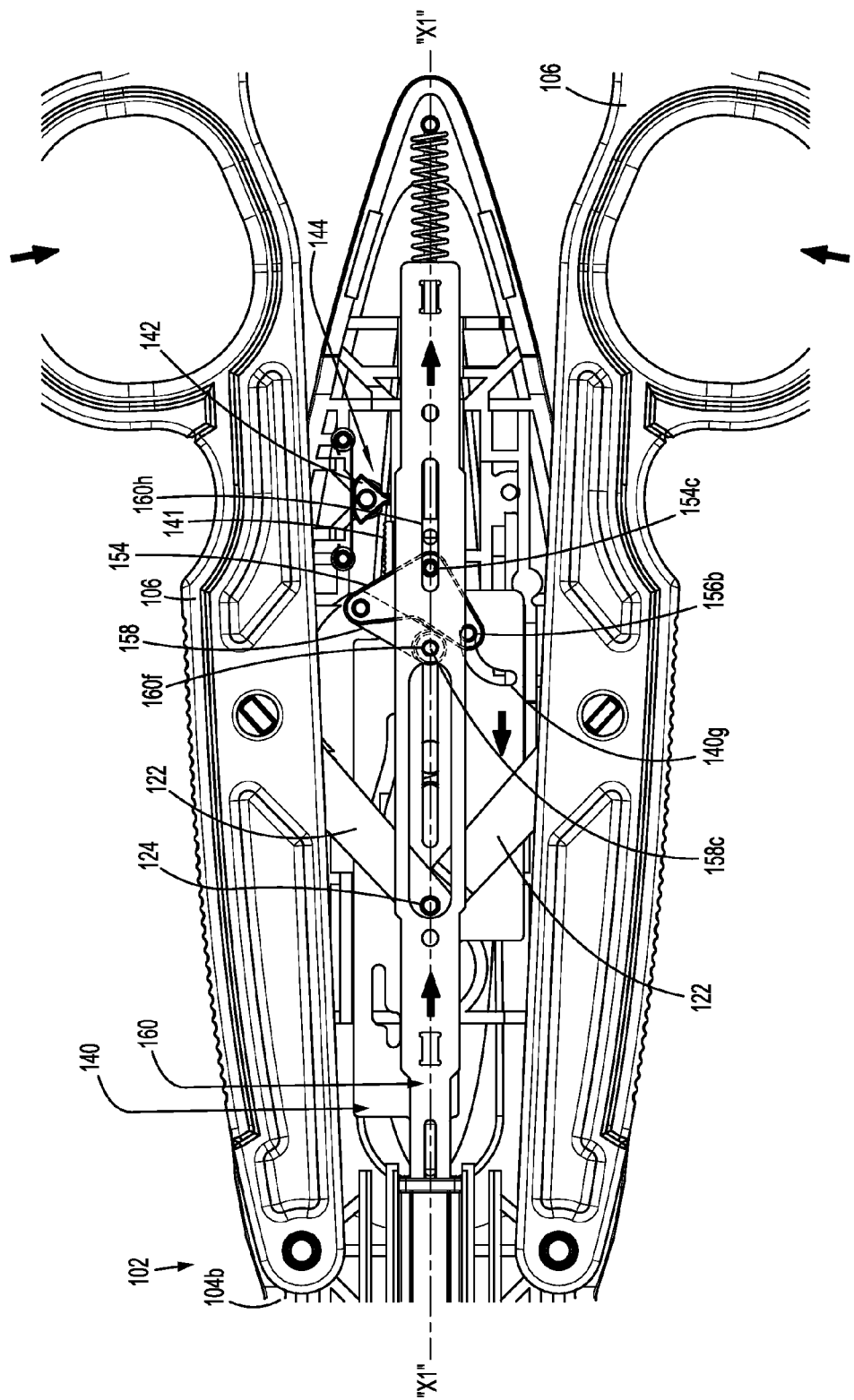
FIG. 41 is a top, plan view of the handle assembly of the surgical clip applier of FIGS. 1 and 2, with the upper housing half removed therefrom and shown following the first complete actuation.
Figure 42:
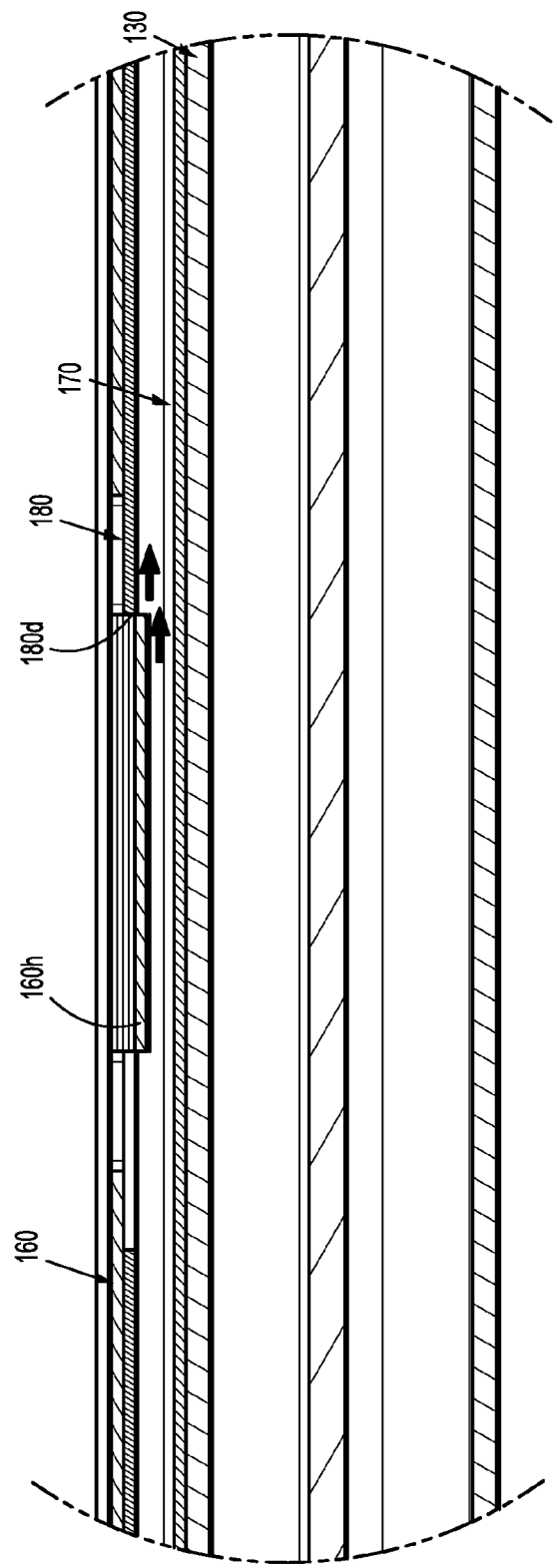
FIG. 42 is an enlarged view of the indicated area 31 of FIG. 28, illustrating a proximal movement of the pusher bar and the walking beam.
Figure 43:
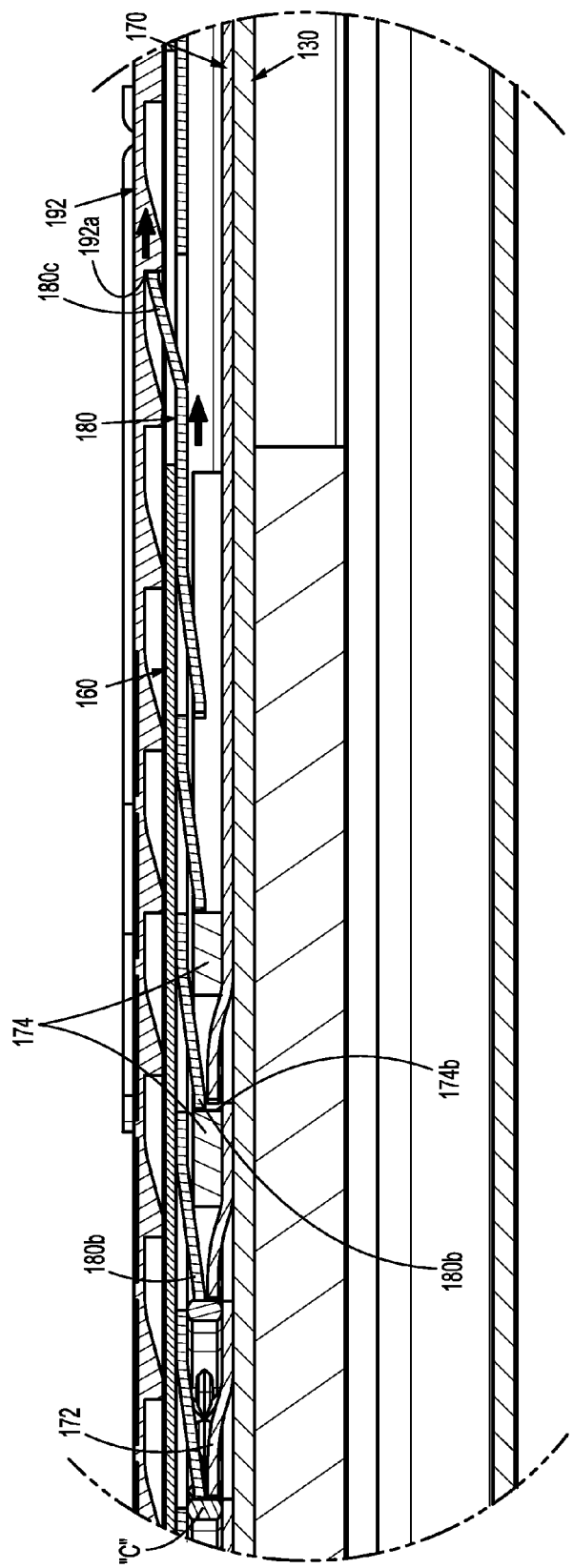
FIG. 43 is an enlarged view of the indicated area 32 of FIG. 29, illustrating a movement of the pusher bar, the walking beam and the clip counter plate.
Figure 44:
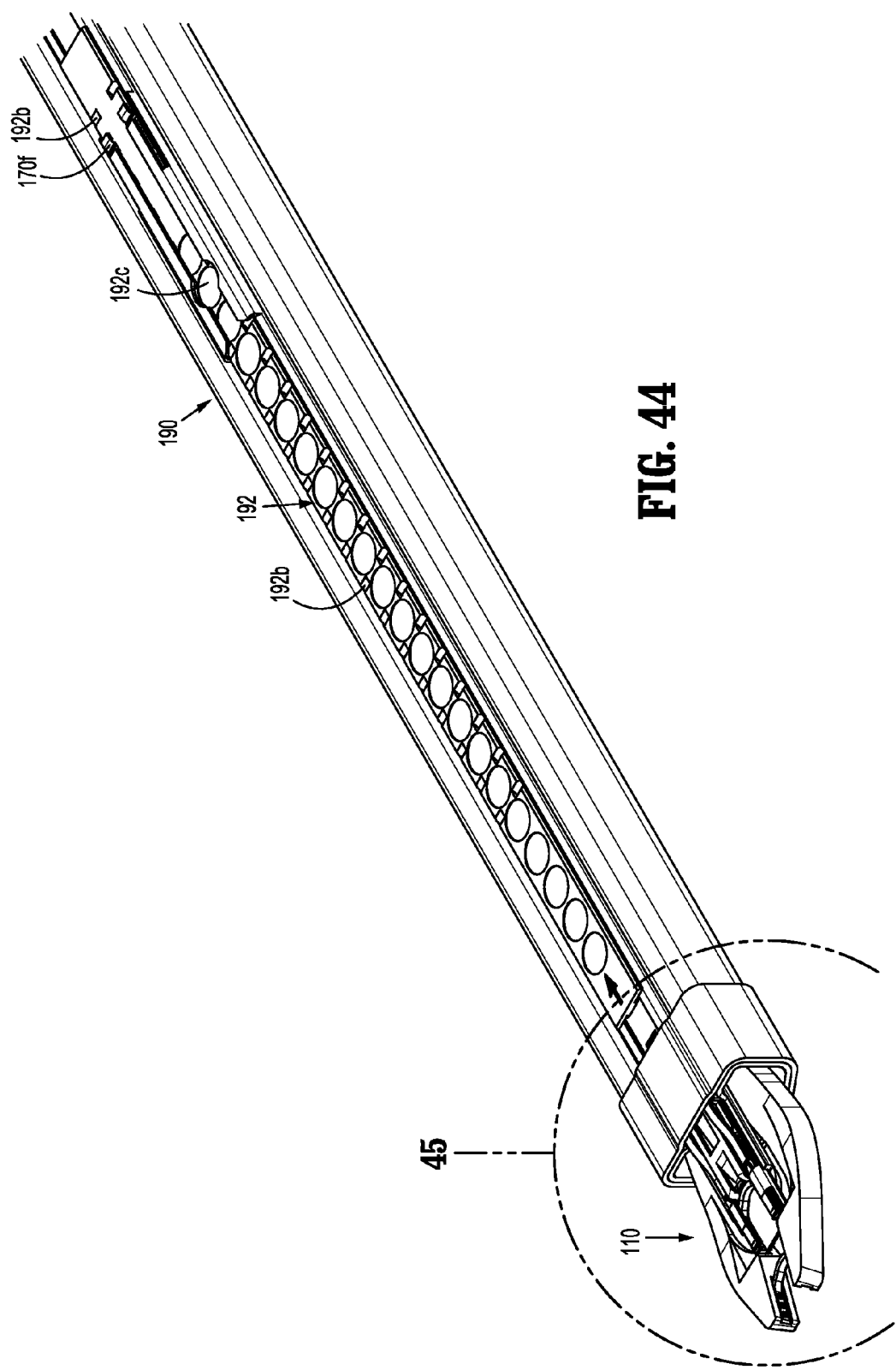
FIG. 44 is a top, perspective view of the distal end of the channel assembly of the surgical clip applier of FIGS. 1 and 2, illustrating the pusher bar, a drive channel and a walking beam, with the pusher bar moving the clip counter plate in a proximal direction.
Figure 45:
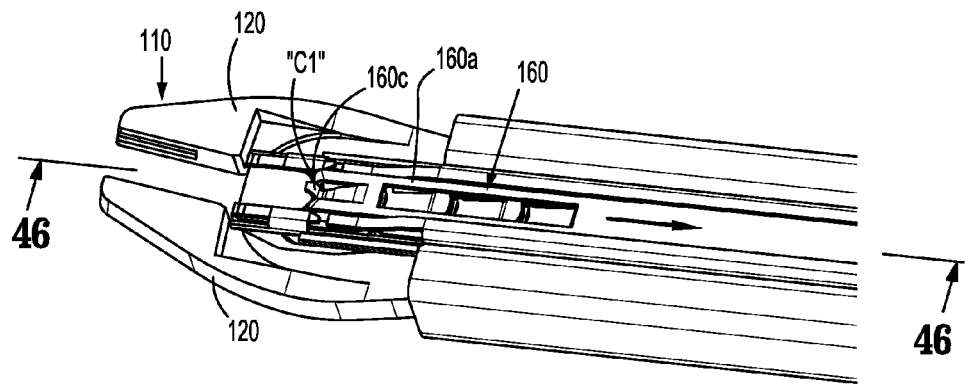
FIG. 45 is an enlarged view of the distal end of the channel assembly of the indicated area of detail 45 of FIG. 44.
Figure 46:
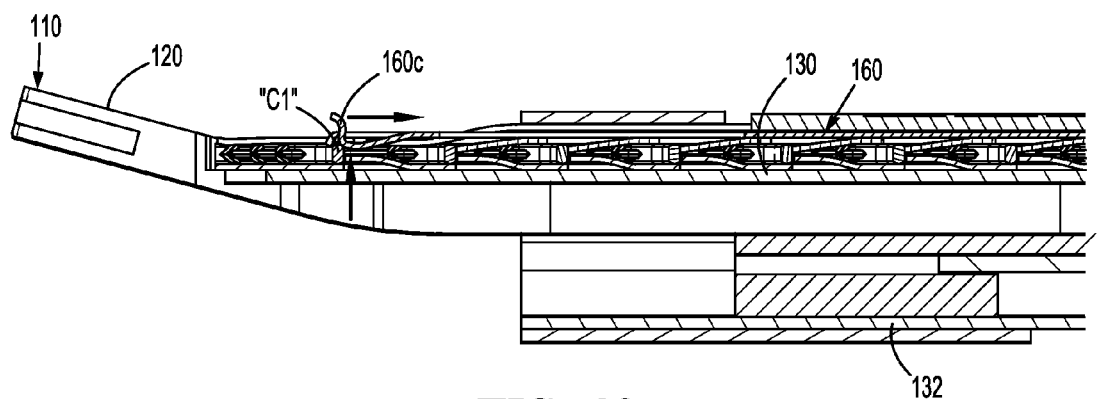
FIG. 46 is a cross-sectional view the distal end of the channel assembly, as taken through 46-46 of FIG. 45.
Figure 47:
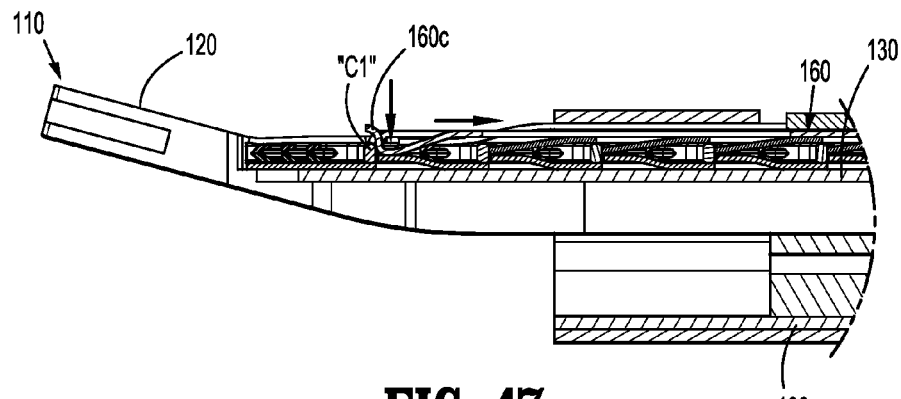
FIG. 47 is a further cross-sectional view of the distal end of the channel assembly, as taken through 46-46 of FIG. 45, illustrating the pusher bar following the first complete squeezing of the handle assembly.

Subsequently, as seen in FIGS. 39-41, as drive channel 140 is moved to a distal-most position, drive linkage system 155 moves from the "home" position to an actuated position. More particularly, advancement of drive channel 140 in a distal direction, in turn, causes crank member 154 to pivot about pivot pin 154c due to the sliding engagement of second pivot pin 156b, which is pinned to second leg 154b of crank member 154, in arcuate slot 140g of drive channel 140.

As crank member 154 is rotated in a first direction, first leg 154a of crank member 154 acts on distal linkage member 158, to move distal linkage member 158 in a proximal direction. Since distal linkage member 158 is pinned to pusher bar 160 by pivot pin 158c, as distal linkage member 158 is moved in a proximal direction, pusher bar 160 is also moved in a proximal direction.

As pusher bar 160 is moved in a proximal direction, tab 160h thereof is moved into contact, following a degree of lost motion, with a proximal end of first slot 180d of walking beam 180, to move walking beam 180 in a proximal direction therewith. As walking beam 180 is moved in a proximal direction, ramps 180b thereof are cammed over the stack of clips "C" so as to be in operative engagement with the next proximal clip in the stack of clips "C". Also, as walking beam 180 is moved in a proximal direction, proximally extending ramp 180c thereof engages notch 192a formed in the underside of counter plate 192 move counter plate 192 in a proximal direction by releasing resilient finger(s) 170f of clip carrier 170 from first proximal notch(es) 192b of counter plate 192 until resilient finger(s) 170f re-engage in the next distal notch(es) 192b of counter plate 192. As counter plate 192 is moved proximally, indicia 192c is moved into registration with a window or indicia formed in a cover mounted to the distal portion of counter 130b to indicate to the user the total initial number of clips available for use.

Also, as pusher bar 160 is moved in a proximal direction, when pusher bar 160 reaches a proximal-most position, pusher 160c thereof is moved to a position proximal of distal-most surgical clip "C1". In this manner, when handles 106 are released, following a complete squeezing, the mechanism is reversed wherein drive channel 140 is moved in a proximal direction and pusher bar 160 is moved in a distal direction. As pusher bar 160 is moved in the distal direction, pusher 160c acts on distal-most clip "C1" to move distal-most clip "C1" in a distal direction, distally out of clip carrier 170, and to load distal-most clip "C1" into channels 120a of jaws 120. As distal-most clip "C1" is moved distally, tangs 171 of clip carrier 170 are deflected or cammed out of engagement with distal-most clip "C1" and return to their un-deflected or un-cammed state to capture a subsequent clip of the stack of clips "C".

During the initial complete release of handles 106, pusher bar 160 is moved distally by an amount sufficient to place distal-most clip "C1" in channels 120a of jaws 120.

Following a complete release of handles 106, pusher bar 160 remains forward such that pusher 160c thereof substantially supports or substantially remains in contact with at least a backspan of the now loaded distal-most clip "C1".

Such a sequence essentially completes the initial priming or loading of a surgical clip "C1" into jaws 120. At such time, surgical clip applier 100 is ready to apply clips to the target surgical site with each complete single squeeze and release of handles 106.

Following the initial priming of surgical clip applier 100 with a surgical clip "C1", as described above, any additional or further complete squeezing of handles 106 will result in the application of the surgical clip "C1", loaded within jaws 120, to the target site, and each subsequent release of handles 106 will result in the loading of a new surgical clip "C" into jaws 120, as will be described in greater detail below.

As seen in FIGS. 39-41, also during any squeeze of handles 106, as drive channel 140 is moved in a distal direction, rack member 141 of ratchet mechanism 144 is moved distally causing the teeth thereof to move into engagement with and over or across a tooth of pawl 142. Once rack member 141 of ratchet mechanism 144 is moved into engagement with pawl 142, drive channel 140 can not return to a home or proximal-most position until rack member 141 has cleared pawl 142 due to a complete squeezing of handles 106.

During any complete squeeze of handles 106, following the initially priming of surgical clip applies 100, as seen in FIGS. 39-47, drive channel 140 is moved distally so as to distally move cam block 143. As cam block 143 is moved distally, cam block 143 acts along an outer camming surface of jaws 120 to approximate jaws 120. Since surgical clip "C1" is disposed in jaws 120, surgical clip "C1" is fully formed when cam block 143 is moved to a distal-most position at a end of the stroke of drive channel 140.

Concomitantly with the distal movement of drive channel 140, during a squeezing of handles 106, pusher bar 160 is moved proximally, as described above. As pusher bar 160 is moved proximally, pusher bar 160 acts on walking beam 180, as described above, to also move walking beam 180 in a proximal direction.

As described above, when walking beam 180 is moved to a proximal-most position, ramps 180b thereof are cammed over the stack of clips "C" so as to be in operative engagement with the next proximal clip in the stack of clips "C".

Also as described above, as walking beam 180 is moved proximally, walking beam 180 acts on counter plate 192, as described above, to also move counter plate 192 in a proximal direction until resilient finger(s) 170f of clip carrier 170 re-engage in the next distal notches) 192b of counter plate 192.

Additionally, as described above, when walking beam 180 is moved to a proximal-most position, ramps 180b thereof are cammed over a distal edge of clip follower 174 such that the next distal ramp 180b of walking beam 180 is disposed in window 174b of clip follower 174. Clip follower 174 is prevented from sliding proximally due to the engagement of clip follower 174 against ramps 172 of clip carrier 170.

Referring now to FIGS. 48-53, during an opening or release of handles 106, distal ends 122a of link members 122 are caused to be moved proximally relative to housing 104. As distal ends 122a of link members 122 are moved proximally, drive pin 124 is caused to be moved proximally thereby transmitting proximal axial movement to drive channel 140 and, in turn, distal axially movement of pusher bar 160. The proximal movement of drive channel 140 is facilitated by the constriction of biasing members 146. Alternatively, the release of handles 106 results in biasing member 146 withdrawing drive channel 140 in a proximal direction.

As drive channel 140 is moved proximally, the distal edge of cam block 143 is retracted and disengages from against the caroming surfaces of jaws 120 thus freeing jaws 120 for separation from one another to receive another surgical clip "C" therebetween.

Additionally, as drive channel 140 is moved proximally, during a release of handles 106 (i.e., a return stroke), to re-load surgical clip applier 100 with a new/next surgical clip "C", distal ends 122a of link members 122 are moved proximally relative to housing 104. As distal ends 122a of link members 122 are moved proximally, drive pin 124 is moved proximally thereby transmitting proximal axial movement to drive channel 140.

Figure 48:
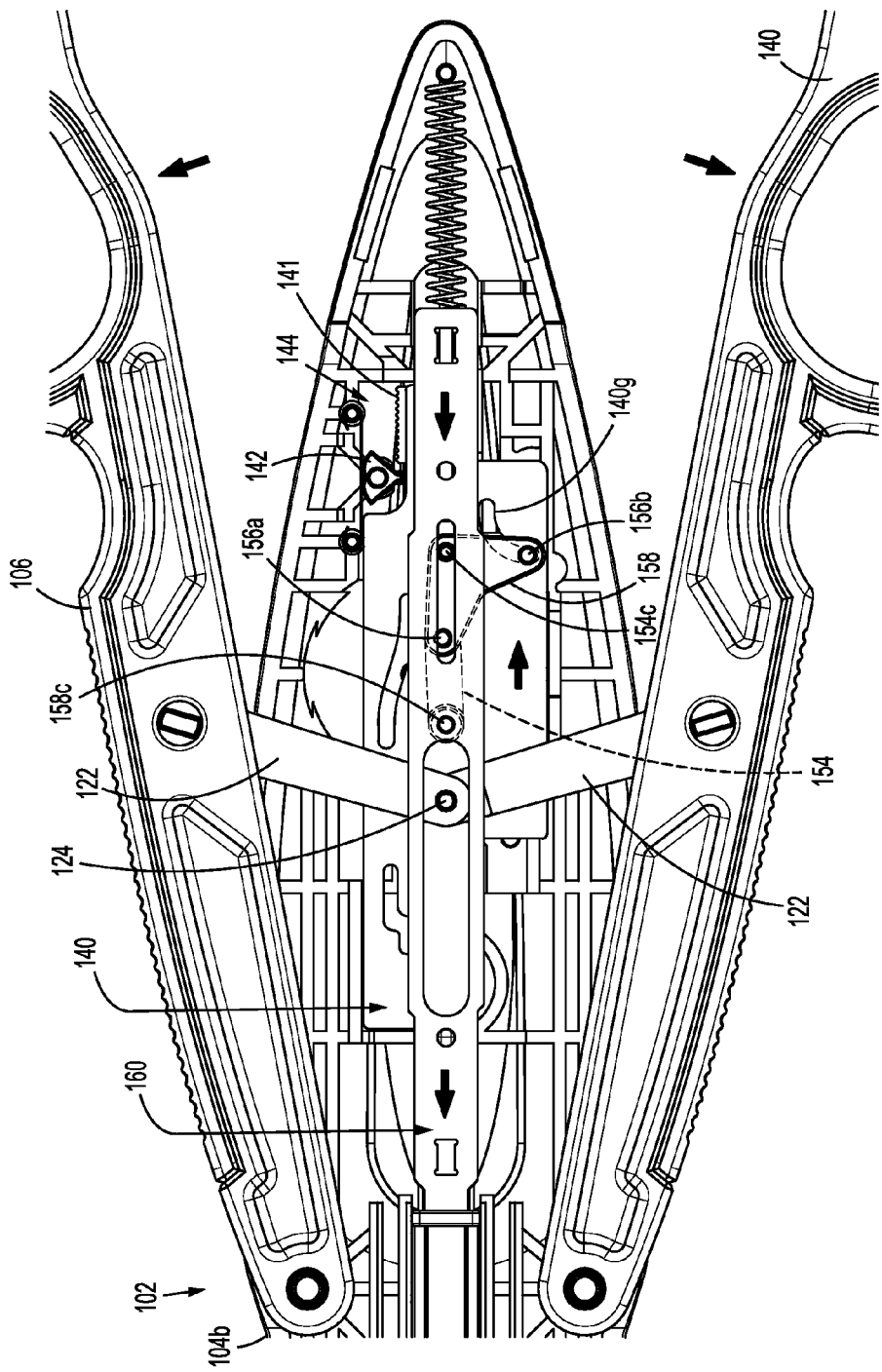
FIG. 48 is a top, plan view of the handle assembly of the surgical clip applier of FIGS. 1 and 2, with the upper housing half and the pusher stabilizer removed therefrom and shown during a return stroke.
Figure 51:
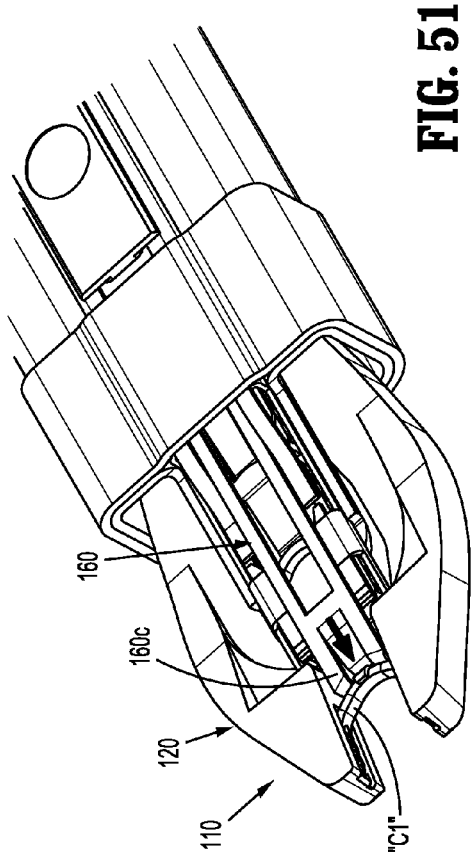
FIG. 51 is a top, perspective view of the distal end of the channel assembly, illustrating the pusher bar moving a distal-most clip into the jaws.
Figure 52:
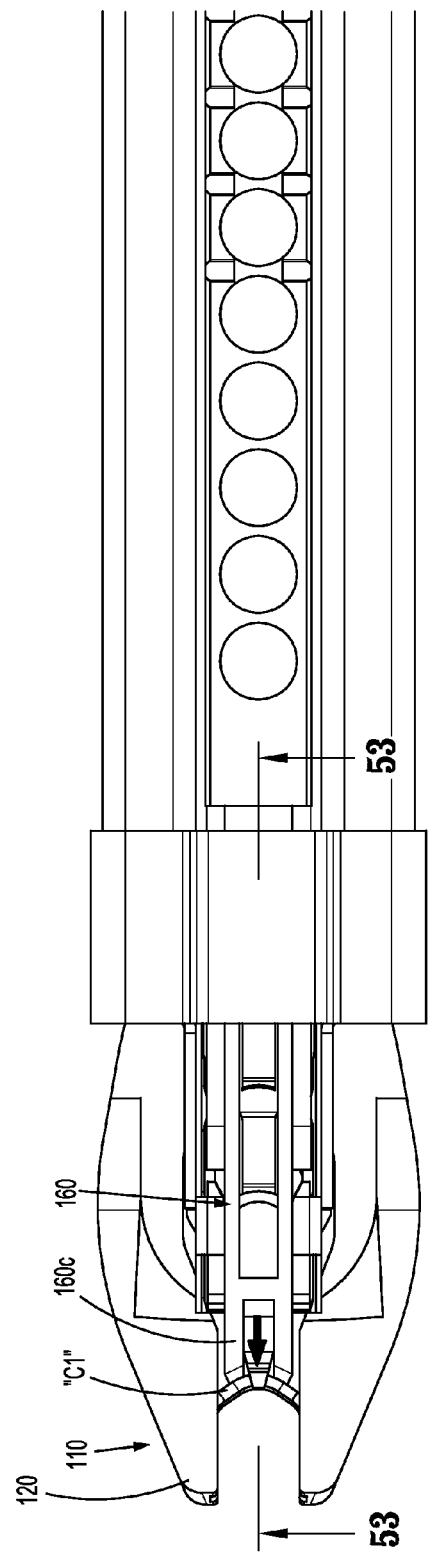
FIG. 52 is a top, plan view of the distal end of the channel assembly, illustrating the pusher bar moving a distal-most clip into the jaws.
Figure 53:
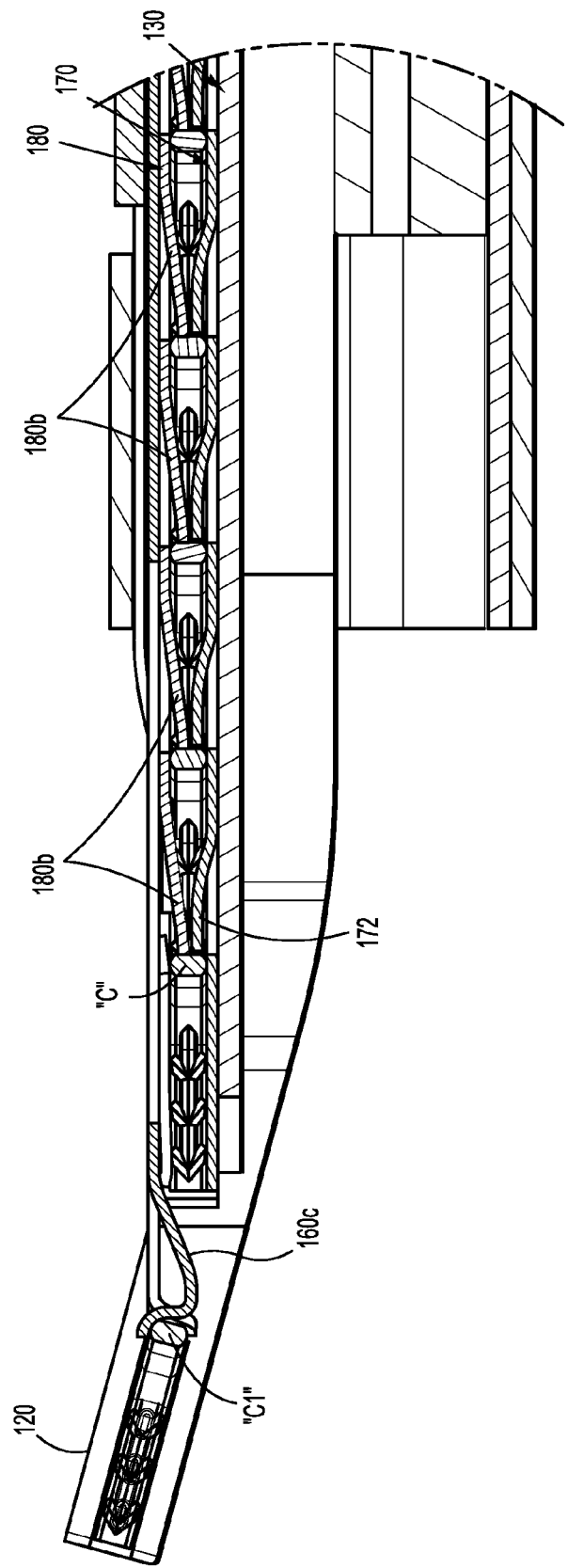
FIG. 53 is a cross-sectional view the distal end of the channel assembly, as taken through 53-53 of FIG. 52.

Subsequently, as seen in FIG. 48, as drive channel 140 is moved to a distal-most position, drive linkage system 155 moves from the actuated position to the "home" position. More particularly, retraction of drive channel 140 in a proximal direction, in turn, causes crank member 154 to pivot about pivot pin 154c due to the sliding engagement of second pivot pin 156b, which is pinned to second leg 154b of crank member 154, in arcuate slot 140g of drive channel 140.

As crank member 154 is rotated in a second direction (opposite the first direction), first leg 154a of crank member 154 acts on distal linkage member 158, to move distal linkage member 158 is a distal direction. Since distal linkage member 158 is pinned to pusher bar 160 by pivot pin 158c, as distal linkage member 158 is moved in a distal direction, pusher bar 160 is also moved in a distal direction.

As pusher bar 160 is moved in a distal direction, tab 160h thereof is moved into contact, following a degree of lost motion, with a front end of first slot 180d of walking beam 180, to move walking beam 180 in a distal direction therewith. As walking beam 180 is moved in a distal direction, ramps 180b thereof engage respective surgical clips of the stack of clips "C" so as to distally advance the surgical clips remaining in the stack of clips "C". Additionally, as walking beam 180 is moved in a distal direction to distally advance the surgical clips remaining in the stack of clips "C", the surgical clips are cammed over or passed ramps 172 of clip carrier 170. As the stack of clips "C" is advanced distally, the stack of clips is held in an axial position by tangs 171 of clip carrier 170.

Also, as walking beam 180 is moved distally, ramps 180b of walking beam 180 engage in window 174b of clip follower 174 and is thus urged distally a given distance.

Also, as walking beam 180 is moved in a distal direction, proximally extending ramp 180c thereof cams over notch 192a formed in the underside of counter plate 192 to come into operative engagement with the next distal notch 192a of counter plate 192, wherein resilient finger(s) 170f of clip carrier 170 maintain a axial position of counter plate 192 due to their engagement in the next distal notch(es) 192b of counter plate 192.

Also, as pusher bar 160 is moved in a distal direction, when pusher bar 160 reaches a distal-most position, pusher 160c thereof has moved a next distal-most clip "C1" of the stack of clips "C", distally out of clip carrier 170, into channels 120a of jaws 120. As next distal-most clip "C1" is moved distally, tangs 171 of clip carrier 170 are deflected or cammed out of engagement with distal-most clip "C1" and return to their un-deflected or un-cammed state to capture a subsequent clip of the stack of clips "C".

Following a complete release of handles 106, pusher bar 160 is moved distally by an amount sufficient to place distal-most clip "C1" in channels 120a of jaws 120. Also following a complete release of handles 106, pusher bar 160 remains forward such that pusher 160c thereof substantially supports or substantially remains in contact with at least a backspan of the now loaded distal-most clip "C1".

Figure 54:
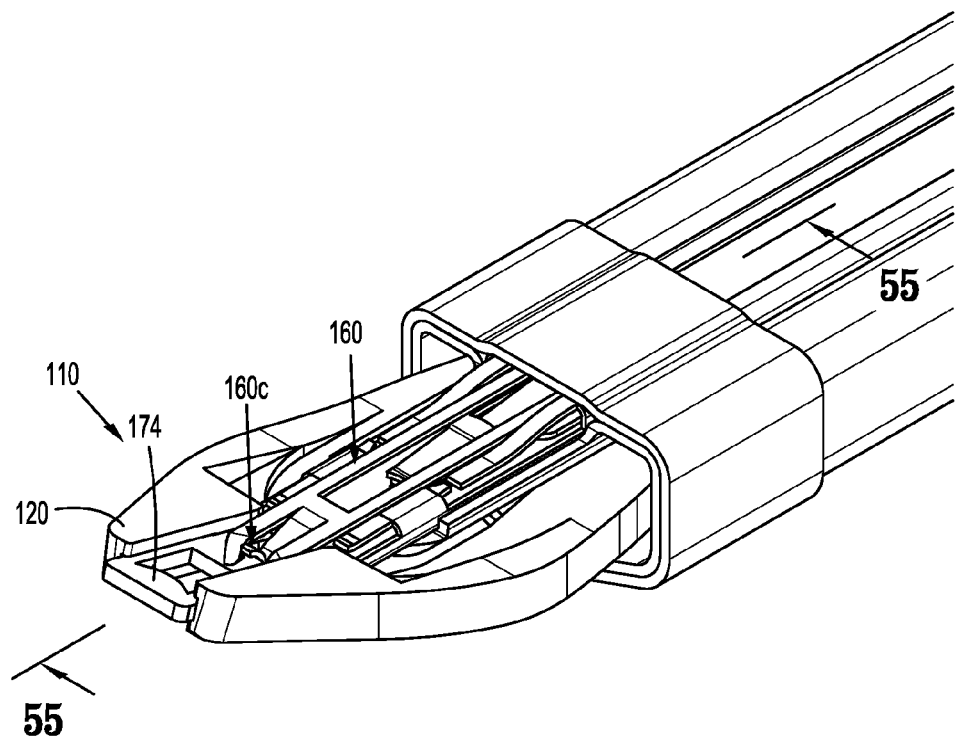
FIG. 54 is a top, perspective view of the distal end of the channel assembly, illustrating the pusher bar moving the clip follower into the jaws to lock out the clip applier.
Figure 55:
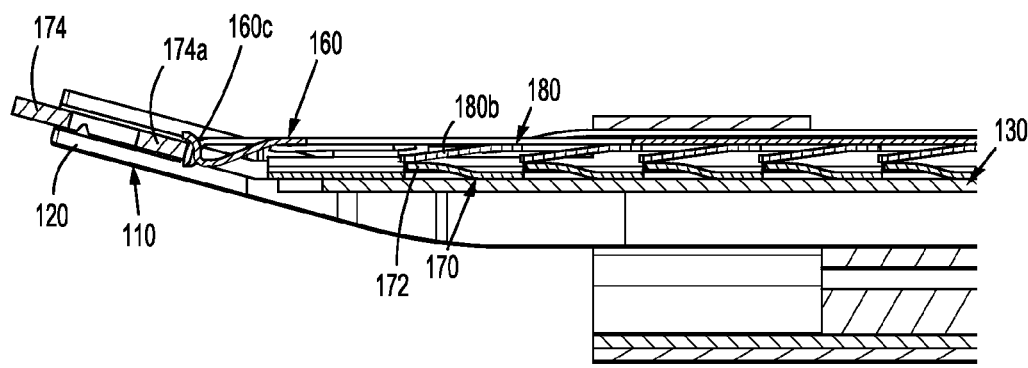
FIG. 55 is a cross-sectional view the distal end of the channel assembly, as taken through 55-55 of FIG. 54.

Turning now to FIGS. 54 and 55, following a firing of the last clip of the stack of clips "C", clip follower 174 has been distally advanced by the reciprocating axial movement of walking beam 180 (as described above) such that pusher 160c of pusher bar 160 may now come into engagement with body portion 174a of clip follower 174 to distally advance clip follower 174 into jaws 120. Since clip follower 174 is disposed within jaws 120, as jaws 120 are approximated, upon any subsequent squeezing of handles 106, as drive channel 140 and cam block 143 are advanced distally, clip follower 174 prevents jaws 120 from approximating. However, since drive channel 140 has advanced distally by some degree, rack member 141 of ratchet mechanism 144 has also been moved distally causing the teeth thereof to move into engagement with tooth of pawl 142. As mentioned above, once rack member 141 of ratchet mechanism 144 is moved into engagement with pawl 142, drive channel 140 can not return to a home or proximal-most position until rack member 141 has cleared pawl 142 due to a complete squeezing of handles 106. However, handles 106 are prevented from being squeezed completely due to the presence of clip follower 174 in jaws 120, thus effectively locking out clip applies 100.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical clip applier, comprising:
a housing;
at least one handle pivotably connected to the housing;
a channel assembly extending distally from the housing;
a clip carrier disposed within the channel assembly defining a channel, the clip carrier including a plurality of distally oriented ramps extending into the clip channel;
a plurality of clips slidably disposed within the channel of the clip carrier;
a clip counter plate slidably supported in the channel assembly, the clip counter plate including a plurality of discrete indicia, wherein a selected one of the plurality of discrete indicia is a discernable indicia from the remainder of the discrete indicia and wherein the clip counter plate is configured and adapted to display a change in status of the clip applier upon each complete actuation of the at least one handle; and
a walking beam reciprocally disposed within the channel assembly and overlying the clip carrier, the walking beam being operatively connected to the at least one handle for reciprocal movement upon actuation of the at least one handle, wherein the clip counter plate defines a series of recesses formed in a first surface thereof, and wherein the walking beam includes a tab extending from a surface thereof and being dimensioned for receipt in each of the series of recesses formed in the clip counter plate, wherein as the walking beam moves, the tab engages the clip counter plate to move the clip counter plate and change the selected one of the plurality of discrete indicia that is the discernable indicia from the remainder of the discrete indicia.

2. The clip applier according to claim 1, wherein each indicia of the plurality of discrete indicia relates to a corresponding quantity of clips of the plurality of clips contained in the clip applier.

3. The clip applier according to claim 1, wherein the discernable indicia is visible through the clip channel.

4. The clip applier according to claim 1, further comprising a clip pusher bar reciprocally positioned within at least one of the housing and the channel assembly, the pusher bar having a first end operatively connected to the at least one handle and a second end defining a pusher, the pusher bar being movable away from a pair of jaws as the at least one handle is actuated by an initial amount in order move the pusher behind a distal-most clip stored in the channel of the clip carrier, and said pusher bar being configured and adapted to move towards the pair of jaws as the at least one handle is returned to a home position to move the distal-most clip between the pair of jaws.

5. The clip applier according to claim 4, further comprising a clip follower slidably disposed within the channel of the clip carrier and disposed proximally of the plurality of clips, the clip follower being configured and adapted for selective engagement with the clip carrier and the walking beam, wherein the clip follower is configured and adapted to urge the plurality of clips, in a distal direction relative to the clip carrier, upon reciprocal movement of the walking beam.

6. The clip applier according to claim 5, wherein the walking beam includes a plurality of distally oriented ramps extending into the clip channel, wherein the distally oriented ramps of the walking beam are configured to selectively engage a first aperture defined in the clip follower and urge the clip follower distally upon distal movement of the walking beam, and wherein the distally oriented ramps of the clip carrier are configured to selectively engage a second aperture defined in the clip follower to stop proximal movement of the clip follower upon proximal movement of the walking beam.

7. The clip applier according to claim 5, wherein the clip follower functions as a lockout when the clip follower is advanced by the walking beam to a position between the pair of jaws.

8. The clip applier according to claim 7, wherein when the clip follower is positioned between the pair of jaws, the clip follower prevents the pair of jaws from completely closing and thus prevents the clip applier from completing a full closing stroke.

9. The clip applier according to claim 4, wherein the clip pusher bar is connected to the walking beam, wherein axial translation of the clip pusher bar results in concomitant axial translation of the walking beam.

10. The clip applier according to claim 9, wherein the clip pusher bar and the walking beam are configured and connected to one another such that a delay is provided between the axial translation of the clip pusher bar and the axial translation of the walking beam.

11. The clip applier according to claim 4, further comprising a drive linkage system configured to proximally move the pusher bar upon an actuation of the at least one handle, and configured to distally move the pusher bar upon a subsequent release of the at least one handle.

12. The clip applier according to claim 11, further comprising a drive channel translatably slidably disposed within at least one of the housing and the channel assembly, the drive channel having a first end operatively connected to the at least one handle and a second end configured and dimensioned to selectively engage said pair of jaws to effectuate closure of the pair of jaws;
the drive channel being moved towards the jaw assembly as the at least one handle is moved in a first direction to move the second end of the drive channel against the pair of jaws to close the pair of jaws;
the drive channel being moved away from the jaw assembly as the at least one handle is moved in a second direction, opposite the first direction, to move the second end of the drive channel away from the jaw assembly to allow the pair of jaws to open.

13. The clip applier according to claim 12, wherein the drive linkage system includes:
a distal linkage member having a first end pivotally connected to the pusher bar; and
a crank member pivotally supported in the housing, the crank member being substantially L-shaped and having a first leg pivotally connected to a second end of the distal linkage member, and having a second leg slidably connected in an actuate channel formed in the drive channel,
wherein distal movement of the drive channel causes the second leg of the crank member to slidably translate through an arcuate slot, thereby causing the crank member to rotate, thereby causing the first leg to rotate, thereby causing the distal linkage member to move proximally, and thereby causing the pusher bar to move proximally.

14. The clip applier according to claim 1, further comprising a jaw assembly including a pair of jaws extending from an end of the channel assembly, opposite the housing, the jaw assembly adapted to accommodate a clip therein and being operable to effect formation of a clip in response to movement of the at least one handle.

* * * * *